(12) United States Patent
Persson et al.

(10) Patent No.: US 7,695,935 B2
(45) Date of Patent: *Apr. 13, 2010

(54) NUCLEIC ACIDS ENCODING HUMAN COAGULATION FVII POLYPEPTIDES

(75) Inventors: Egon Persson, Malmø (SE); Ole Hvilsted Olsen, Brønshøj (DK)

(73) Assignee: Novo Nordisk Healthcare A/G, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/486,586

(22) Filed: Jul. 14, 2006

(65) Prior Publication Data

US 2006/0252129 A1 Nov. 9, 2006

Related U.S. Application Data

(62) Division of application No. 09/951,121, filed on Sep. 13, 2001.

(60) Provisional application No. 60/236,455, filed on Sep. 29, 2000.

(30) Foreign Application Priority Data

Sep. 13, 2000 (DK) ............................... 2000 01361

(51) Int. Cl.
*C12P 21/06* (2006.01)
(52) U.S. Cl. .................. 435/69.1; 435/7.1; 435/320.1; 435/325; 435/6
(58) Field of Classification Search ...................... None
See application file for complete search history.

(56) References Cited

U.S. PATENT DOCUMENTS

| | | | |
|---|---|---|---|
| 5,288,629 A | 2/1994 | Berkner | |
| 5,580,560 A | 12/1996 | Nicolaisen et al. | ........ 424/94.64 |
| 5,874,407 A | 2/1999 | Kelley et al. | ................. 514/12 |
| 5,994,296 A | 11/1999 | Ruf et al. | ....................... 514/2 |
| 2003/0096338 A1 | 5/2003 | Pedersen et al. | ........... 435/69.1 |
| 2003/0130191 A1 | 7/2003 | Persson et al. | ................ 514/12 |
| 2003/0170863 A1 | 9/2003 | Persson et al. | |
| 2004/0033566 A1 | 2/2004 | Ruf et al. | |

FOREIGN PATENT DOCUMENTS

| | | |
|---|---|---|
| EP | 0 200 421 B1 | 4/1986 |
| WO | WO 01/58935 A2 | 8/2001 |
| WO | WO 01/75086 A2 | 10/2001 |
| WO | WO 01/82943 A2 | 11/2001 |
| WO | WO 01/85198 A1 | 11/2001 |
| WO | WO2004/029090 | 4/2004 |

OTHER PUBLICATIONS

U.S. Appl. No. 60/184,036.
U.S. Appl. No. 10/415,963.
International Search Report Aug. 25, 2003.
International Search Report Feb. 5, 2004.
Peyvandi et al., Thromb Haemost, vol. 84, pp. 250-257 (2000).
Peyvandi et al., Thromb Haemost, vol. 88, pp. 750-755 (2002).
Fair, Kumar, Abstract Europ Journ of Biochem, vol. 217 (2), pp. 509-518 (1993).
Soejima et al., Journ of Bio Chem, vol. 276 (20), pp. 17229-17235 (2001).
O'Brien, D.P. et al., Surface Plasmon Resonance Studies of the Interaction between Factor VII and Tissue Factor. Demonstartion of Defcetive Tissue Factor Binding in a Variant FVII Molecule (FVII-R79Q), Biochemistry, vol. 33, pp. 14161-14169 (1994).
Persson, E. et al., Substitution of Aspartic Acid for Methionine-306 in Factor VIIa Abolishes the Allosteric Linkage between the Active Site and the Binding Interface with Tissue Factor, Biochemistry, vol. 40, pp. 3251-3256 (2001).
Petersen, L.C. et al., Binding of Zn2+ to a Ca2+ Loop Allosterically Attenuates the Activity of Factor VIIa and Reduces Its Affinity for Tissue Factor [In Process Citation], Protein Science, vol. 9, pp. 859-866 (2000).
Sommer, S.S., Assessing the Underlying Pattern of Human Germline Mutations: Lessons from the Factor IX Gene, The Faseb Journal, vol. 6, pp. 2767-2774 (1992).
Sridhara, S. et al., Activation of a Recombinant Human Factor VII Structural Analogue Alters Its Affinity of Binding to Tissue Factor, American Journal of Hematology, vol. 53, pp. 66-71 (1996).
Kimchi-Sarfaty et al., Science, vol. 315, pp. 526-528 (2007).
Bowie et al., Science, vol. 247, pp. 1306-1310 (1990).
Skolnick et al., Tibtech, vol. 18, pp. 34-39 (2000).
Wells, Biochemistry, vol. 29, pp. 8509-8517 (1990).
Office Action for U.S. Appl. No. 11/111,663 sent from the USPTO on May 13, 2009.

*Primary Examiner*—Hope A Robinson
(74) *Attorney, Agent, or Firm*—Reza Green

(57) ABSTRACT

The present invention relates to novel human coagulation Factor VIIa variants having coagulant activity as well as nucleic acid constructs encoding such variants, vectors and host cells comprising and expressing the nucleic acid, pharmaceutical compositions, uses and methods of treatment.

11 Claims, 2 Drawing Sheets

FIGURE 1 - the amino acid sequence of native human coagulation Factor VII

```
  Ala Asn Ala Phe Leu Xaa Xaa Leu Arg Pro Gly Ser Leu Xaa Arg Xaa
  1               5                   10              15

Cys Lys Xaa Xaa Gln Cys Ser Phe Xaa Xaa Ala Arg Xaa Ile Phe Lys
              20              25              30

Asp Ala Xaa Arg Thr Lys Leu Phe Trp Ile Ser Tyr Ser Asp Gly Asp
              35              40              45

Gln Cys Ala Ser Ser Pro Cys Gln Asn Gly Gly Ser Cys Lys Asp Gln
      50              55              60

Leu Gln Ser Tyr Ile Cys Phe Cys Leu Pro Ala Phe Glu Gly Arg Asn
  65              70              75                              80

Cys Glu Thr His Lys Asp Asp Gln Leu Ile Cys Val Asn Glu Asn Gly
              85              90              95

Gly Cys Glu Gln Tyr Cys Ser Asp His Thr Gly Thr Lys Arg Ser Cys
              100             105             110

Arg Cys His Glu Gly Tyr Ser Leu Leu Ala Asp Gly Val Ser Cys Thr
              115             120             125

Pro Thr Val Glu Tyr Pro Cys Gly Lys Ile Pro Ile Leu Glu Lys Arg
      130             135             140

Asn Ala Ser Lys Pro Gln Gly Arg Ile Val Gly Gly Lys Val Cys Pro
  145             150             155                             160

Lys Gly Glu Cys Pro Trp Gln Val Leu Leu Leu Val Asn Gly Ala Gln
              165             170             175

Leu Cys Gly Gly Thr Leu Ile Asn Thr Ile Trp Val Val Ser Ala Ala
              180             185             190

His Cys Phe Asp Lys Ile Lys Asn Trp Arg Asn Leu Ile Ala Val Leu
              195             200             205

Gly Glu His Asp Leu Ser Glu His Asp Gly Asp Glu Gln Ser Arg Arg
              210             215             220
```

```
Val Ala Gln Val Ile Ile Pro Ser Thr Tyr Val Pro Gly Thr Thr Asn
225             230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260             265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305             310                 315                 320

Pro Asn Ile Thr Glu Tyr Met Phe Cys Ala Gly Tyr Ser Asp Gly Ser
                325             330                 335

Lys Asp Ser Cys Lys Gly Asp Ser Gly Gly Pro His Ala Thr His Tyr
            340             345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385             390                 395                 400

Leu Arg Ala Pro Phe Pro
                405
```

SEQUENCE LISTING

<160> NUMBER OF SEQ ID NOS: 17

<210> SEQ ID NO 1
<211> LENGTH: 406
<212> TYPE: PRT
<213> ORGANISM: Human
<220> FEATURE:
<221> NAME/KEY: MISC_FEATURE
<222> LOCATION: (1)..(406)
<223> OTHER INFORMATION: Xaa=gamma carboxyglutamic acid

<400> SEQUENCE: 1

```
Ala Asn Ala Phe Leu Xaa Xaa Leu Arg Pro Gly Ser Leu Xaa Arg Xaa
1               5                   10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80
```

```
Cys Glu Thr His Lys Asp Asp Gln Leu Ile Cys Val Asn Gly Asn Gly
                 85                  90                  95
Gly Cys Glu Gln Tyr Cys Ser Asp His Thr Gly Thr Lys Arg Ser Cys
            100                 105                 110
Arg Cys His Glu Gly Tyr Ser Leu Leu Ala Asp Gly Val Ser Cys Thr
        115                 120                 125
Pro Thr Val Glu Tyr Pro Cys Gly Lys Ile Pro Ile Leu Glu Lys Arg
    130                 135                 140
Asn Ala Ser Lys Pro Gln Gly Arg Ile Val Gly Gly Lys Val Cys Pro
145                 150                 155                 160
Lys Gly Glu Cys Pro Trp Gln Val Leu Leu Leu Val Asn Gly Ala Gln
                165                 170                 175
Leu Cys Gly Gly Thr Leu Ile Asn Thr Ile Trp Val Val Ser Ala Ala
            180                 185                 190
His Cys Phe Asp Lys Ile Lys Asn Trp Arg Asn Leu Ile Ala Val Leu
        195                 200                 205
Gly Glu His Asp Leu Ser Glu His Asp Gly Asp Glu Gln Ser Arg Arg
    210                 215                 220
Val Ala Gln Val Ile Ile Pro Ser Thr Tyr Val Pro Gly Thr Thr Asn
225                 230                 235                 240
His Asp Ile Ala Leu Leu Arg Leu His Gln Pro Val Val Leu Thr Asp
                245                 250                 255
His Val Val Pro Leu Cys Leu Pro Glu Arg Thr Phe Ser Glu Arg Thr
            260                 265                 270
Leu Ala Phe Val Arg Phe Ser Leu Val Ser Gly Trp Gly Gln Leu Leu
        275                 280                 285
Asp Arg Gly Ala Thr Ala Leu Glu Leu Met Val Leu Asn Val Pro Arg
    290                 295                 300
Leu Met Thr Gln Asp Cys Leu Gln Gln Ser Arg Lys Val Gly Asp Ser
305                 310                 315                 320
Pro Asn Ile Thr Glu Tyr Met Phe Cys Ala Gly Tyr Ser Asp Gly Ser
                325                 330                 335
Lys Asp Ser Cys Lys Gly Asp Ser Gly Gly Pro His Ala Thr His Tyr
            340                 345                 350
Arg Gly Thr Trp Tyr Leu Thr Gly Ile Val Ser Trp Gly Gln Gly Cys
        355                 360                 365
Ala Thr Val Gly His Phe Gly Val Tyr Thr Arg Val Ser Gln Tyr Ile
    370                 375                 380
Glu Trp Leu Gln Lys Leu Met Arg Ser Glu Pro Arg Pro Gly Val Leu
385                 390                 395                 400
Leu Arg Ala Pro Phe Pro
                405

<210> SEQ ID NO 2
<211> LENGTH: 34
<212> TYPE: DNA
<213> ORGANISM: Artificial Sequence
<220> FEATURE:
<223> OTHER INFORMATION: Synthetic

<400> SEQUENCE: 2
ccgaattgtg gggggcgcgg tgtgccccaa aggg                              34

<210> SEQ ID NO 3
<211> LENGTH: 34
```

-continued

<212> TYPE: DNA
<213> ORGANISM: Artificial Sequence
<220> FEATURE:
<223> OTHER INFORMATION: Synthetic

<400> SEQUENCE: 3
ccctttgggg cacaccgcgc cccccacaat tcgg                                    34

<210> SEQ ID NO 4
<211> LENGTH: 28
<212> TYPE: DNA
<213> ORGANISM: Artificial Sequence
<220> FEATURE:
<223> OTHER INFORMATION: Synthetic

<400> SEQUENCE: 4 gtgggggca aggactgccc caaagggg                                            28

<210> SEQ ID NO 5
<211> LENGTH: 28
<212> TYPE: DNA
<213> ORGANISM: Artificial Sequence
<220> FEATURE:
<223> OTHER INFORMATION: Synthetic

<400> SEQUENCE: 5
cccctttggg gcagtccttg cccccac                                            28

<210> SEQ ID NO 6
<211> LENGTH: 28
<212> TYPE: DNA
<213> ORGANISM: Artificial Sequence
<220> FEATURE:
<223> OTHER INFORMATION: Synthetic

<400> SEQUENCE: 6 gtgggggca agacgtgccc caaagggg                                            28

<210> SEQ ID NO 7
<211> LENGTH: 28
<212> TYPE: DNA
<213> ORGANISM: Artificial Sequence
<220> FEATURE:
<223> OTHER INFORMATION: Synthetic

<400> SEQUENCE: 7
cccctttggg gcacgtcttg cccccac                                            28

<210> SEQ ID NO 8
<211> LENGTH: 36
<212> TYPE: DNA
<213> ORGANISM: Artificial Sequence
<220> FEATURE:
<223> OTHER INFORMATION: Synthetic

<400> SEQUENCE: 8
gccacggccc tggtgctcca ggtcctcaac gtgccc                                  36

<210> SEQ ID NO 9
<211> LENGTH: 36
<212> TYPE: DNA
<213> ORGANISM: Artificial Sequence
<220> FEATURE:
<223> OTHER INFORMATION: Synthetic

<400> SEQUENCE: 9

```
gggcacgttg aggacctgga gcaccagggc cgtggc                                    36

<210> SEQ ID NO 10
<211> LENGTH: 30
<212> TYPE: DNA
<213> ORGANISM: Artificial Sequence
<220> FEATURE:
<223> OTHER INFORMATION: Synthetic

<400> SEQUENCE: 10
gccctggagc tccaggtcct caacgtgccc                                           30

<210> SEQ ID NO 11
<211> LENGTH: 30
<212> TYPE: DNA
<213> ORGANISM: Artificial Sequence
<220> FEATURE:
<223> OTHER INFORMATION: Synthetic

<400> SEQUENCE: 11
gggcacgttg aggacctgga gctccagggc                                           30

<210> SEQ ID NO 12
<211> LENGTH: 27
<212> TYPE: DNA
<213> ORGANISM: Artificial Sequence
<220> FEATURE:
<223> OTHER INFORMATION: Synthetic

<400> SEQUENCE: 12
gccctggagc tcaaggtcct caacgtg                                              27

<210> SEQ ID NO 13
<211> LENGTH: 27
<212> TYPE: DNA
<213> ORGANISM: Artificial Sequence
<220> FEATURE:
<223> OTHER INFORMATION: Synthetic

<400> SEQUENCE: 13
caccttgagg accttgagct ccagggc                                              27

<210> SEQ ID NO 14
<211> LENGTH: 33
<212> TYPE: DNA
<213> ORGANISM: Artificial Sequence
<220> FEATURE:
<223> OTHER INFORMATION: Synthetic

<400> SEQUENCE: 14
ggctactcgg atggcggcaa ggactcctgc aag                                       33

<210> SEQ ID NO 15
<211> LENGTH: 33
<212> TYPE: DNA
<213> ORGANISM: Artificial Sequence
<220> FEATURE:
<223> OTHER INFORMATION: Synthetic

<400> SEQUENCE: 15
cttgcaggag tccttgccgc catccgagta gcc                                       33

<210> SEQ ID NO 16
<211> LENGTH: 28
<212> TYPE: DNA
<213> ORGANISM: Artificial Sequence
```

```
<220> FEATURE:
<223> OTHER INFORMATION: Synthetic

<400> SEQUENCE: 16
cggatggcag cgcggactcc tgcaaggg                                              28

<210> SEQ ID NO 17
<211> LENGTH: 28
<212> TYPE: DNA
<213> ORGANISM: Artificial Sequence
<220> FEATURE:
<223> OTHER INFORMATION: Synthetic

<400> SEQUENCE: 17
cccttgcagg agtccgcgct gccatccg                                              28
```

US 7,695,935 B2

NUCLEIC ACIDS ENCODING HUMAN COAGULATION FVII POLYPEPTIDES

CROSS-REFERENCE TO RELATED APPLICATIONS

This application is a Divisional of U.S. application Ser. No. 09/951,121 filed on Sep. 13, 2001 and claims priority under 35 U.S.C. 119 of U.S. application Ser. No. 60/236,455 filed on Sep. 29, 2000 and Danish application no. PA 2000 01361 filed on Sep. 13, 2000, the contents of which are fully incorporated herein by reference.

FIELD OF THE INVENTION

The present invention relates to novel human coagulation Factor VIIa variants having coagulant activity as well as nucleic acid constructs encoding such variants, vectors and host cells comprising and expressing the nucleic acid, pharmaceutical compositions, uses and methods of treatment.

BACKGROUND OF THE INVENTION

Blood coagulation is a process consisting of a complex interaction of various blood components (or factors) that eventually gives raise to a fibrin clot. Generally, the blood components, which participate in what has been referred to as the coagulation "cascade", are enzymatically inactive proteins (proenzymes or zymogens) that are converted to proteolytic enzymes by the action of an activator (which itself is an activated clotting factor). Coagulation factors that have undergone such a conversion are generally referred to as "active factors", and are designated by the addition of the letter "a" to the name of the coagulation factor (e.g. Factor VIIa).

Initiation of the haemostatic process is mediated by the formation of a complex between tissue factor, exposed as a result of injury to the vessel wall, and Factor VIIa. This complex then converts Factors IX and X to their active forms. Factor Xa converts limited amounts of prothrombin to thrombin on the tissue factor-bearing cell. Thrombin activates platelets and Factors V and VIII into Factors Va and VIIIa, both cofactors in the further process leading to the full thrombin burst. This process includes generation of Factor Xa by Factor IXa (in complex with factor VIIIa) and occurs on the surface of activated platelets. Thrombin finally converts fibrinogen to fibrin resulting in formation of a fibrin clot. In recent years Factor VII and tissue factor have been found to be the main initiators of blood coagulation.

Factor VII is a trace plasma glycoprotein that circulates in blood as a single-chain zymogen. The zymogen is catalytically inactive. Single-chain Factor VII may be converted to two-chain Factor VIIa by Factor Xa, Factor XIIa, Factor IXa, Factor VIIa or thrombin in vitro. Factor Xa is believed to be the major physiological activator of Factor VII. Like several other plasma proteins involved in haemostasis, Factor VII is dependent on Vitamin K for its activity, which is required for the gamma-carboxylation of multiple glutamic acid residues that are clustered close to the amino terminus of the protein. These gamma-carboxylated glutamic acids are required for the metal ion-induced interaction of Factor VII with phospholipids. The conversion of zymogen Factor VII into the activated two-chain molecule occurs by cleavage of an internal $Arg_{152}$-$Ile_{153}$ peptide bond. In the presence of tissue factor, phospholipids and calcium ions, the two-chain Factor VIIa rapidly activates Factor X or Factor IX by limited proteolysis.

It is often desirable to stimulate or improve the coagulation cascade in a subject. Factor VIIa has been used to control bleeding disorders that have several causes such as clotting factor deficiencies (e.g. haemophilia A and B or deficiency of coagulation Factors XI or VII) or clotting factor inhibitors. Factor VIIa has also been used to control excessive bleeding occurring in subjects with a normally functioning blood clotting cascade (no clotting factor deficiencies or inhibitors against any of the coagulation factors). Such bleeding may, for example, be caused by a defective platelet function, thrombocytopenia or von Willebrand's disease. Bleeding is also a major problem in connection with surgery and other forms of tissue damage.

European Patent No. 200,421 (ZymoGenetics) relates to the nucleotide sequence encoding human Factor VII and the recombinant expression of Factor VII in mammalian cells.

Dickinson et al. (Proc. Natl. Acad. Sci. USA (1996) 93, 14379-14384) relates to Factor VII variants wherein Lys157, Val158, Glu296, Met298, Asp334, Ser336 or Lys337 have been individually replaced by Ala.

Iwanaga et al. (Thromb. Haemost. (supplement August 1999), 466, abstract 1474) relates to FVIIa variants wherein residues 316-320 are deleted or residues 311-322 are replaced with the corresponding residues from trypsin.

There is, however, still a need for variants of Factor VIIa having coagulant activity, variants with high activity that can be administered at relatively low doses, and variants which do not produce the undesirable side effects such as systemic activation of the coagulation system and bleeding, respectively, associated with conventional therapies.

DESCRIPTION OF THE INVENTION

The invention provides coagulation Factor VIIa polypeptides with coagulant activity.

In a first aspect, the invention provides a Factor VII polypeptide comprising the amino acid sequence of SEQ ID NO:1 or a variant thereof, wherein at least the amino acid corresponding to the Lys at position 157 of SEQ ID NO:1 has been replaced by a different amino acid; with the proviso that the variant is not FVII(Ala157).

In a second aspect, the invention provides a Factor VII polypeptide comprising the amino acid sequence of SEQ ID NO:1 or a variant thereof, wherein at least the amino acid corresponding to the Lys at position 337 of SEQ ID NO:1 has been replaced by a different amino acid; with the proviso that the variant is not FVII(Ala337).

In a third aspect, the invention provides a Factor VII polypeptide comprising the amino acid sequence of SEQ ID NO:1 or a variant thereof, wherein at least the amino acid corresponding to the Asp at position 334 of SEQ ID NO:1 has been replaced by a different amino acid; with the proviso that the variant is not FVII(Ala334).

In a further aspect, the invention provides a Factor VII polypeptide comprising the amino acid sequence of SEQ ID NO:1 or a variant thereof, wherein at least the amino acid corresponding to the Ser at position 336 of SEQ ID NO:1 has been replaced by a different amino acid; with the proviso that the variant is not FVII(Ala336).

In a further aspect, the invention provides a Factor VII polypeptide comprising the amino acid sequence of SEQ ID NO:1 or a variant thereof, wherein at least the amino acid corresponding to the Val at position 158 of SEQ ID NO:1 has been replaced by a different amino acid; with the proviso that the variant is not FVII(Ala158).

In a further aspect, the invention provides a Factor VII polypeptide comprising the amino acid sequence of SEQ ID NO:1 or a variant thereof, wherein at least the amino acid corresponding to the Glu at position 296 of SEQ ID NO:1 has been replaced by a different amino acid; with the proviso that the variant is not FVII(Ala296).

In a further aspect, the invention provides a Factor VII polypeptide comprising the amino acid sequence of SEQ ID NO:1 or a variant thereof, wherein at least the amino acid corresponding to the Met at position 298 of SEQ ID NO:1 has been replaced by a different amino acid; with the proviso that the variant is not FVII(Ala298).

In a further aspect, the invention provides a Factor VII polypeptide with the sequence of SEQ ID NO:1, wherein one amino acid independently selected from the group consisting of the Lys at position 157, the Lys at position 337, the Asp at position 334, the Ser at position 336, the Val at position 158, the Glu at position 296 and the Met at position 298 of SEQ ID NO:1 has been replaced by a different amino acid; with the proviso that the variant is not FVII(Ala157), FVII(Ala334), FVII(Ala336), FVII(Ala337), FVII(Ala158), FVII(Ala296) or FVII(Ala298).

In a further aspect, the invention provides a Factor VII polypeptide with the sequence of SEQ ID NO:1, wherein two amino acids independently selected from the group consisting of the Lys at position 157, the Lys at position 337, the Asp at position 334, the Ser at position 336, the Val at position 158, the Glu at position 296 and the Met at position 298 of SEQ ID NO:1 have been replaced by different amino acids.

In a further aspect, the invention provides a Factor VII polypeptide with the sequence of SEQ ID NO:1, wherein three amino acids independently selected from the group consisting of the Lys at position 157, the Lys at position 337, the Asp at position 334, the Ser at position 336, the Val at position 158, the Glu at position 296 and the Met at position 298 of SEQ ID NO:1 have been replaced by different amino acids.

In a further aspect, the invention provides a Factor VII polypeptide with the sequence of SEQ ID NO:1, wherein four amino acids independently selected from the group consisting of the Lys at position 157, the Lys at position 337, the Asp at position 334, the Ser at position 336, the Val at position 158, the Glu at position 296 and the Met at position 298 of SEQ ID NO:1 have been replaced by different amino acids.

In a further aspect, the invention provides a Factor VII polypeptide with the sequence of SEQ ID NO:1, wherein five amino acids independently selected from the group consisting of the Lys at position 157, the Lys at position 337, the Asp at position 334, the Ser at position 336, the Val at position 158, the Glu at position 296 and the Met at position 298 of SEQ ID NO:1 have been replaced by different amino acids.

In a further aspect, the invention provides a Factor VII polypeptide with the sequence of SEQ ID NO:1, wherein six amino acids independently selected from the group consisting of the Lys at position 157, the Lys at position 337, the Asp at position 334, the Ser at position 336, the Val at position 158, the Glu at position 296 and the Met at position 298 of SEQ ID NO:1 have been replaced by different amino acids.

In a further aspect, the invention provides a Factor VII polypeptide with the sequence of SEQ ID NO:1, wherein the amino acids consisting of the Lys at position 157, the Lys at position 337, the Asp at position 334, the Ser at position 336, the Val at position 158, the Glu at position 296 and the Met at position 298 of SEQ ID NO:1 have been replaced by different amino acids.

In a further aspect, the invention provides a coagulation Factor VII variant, wherein one or more of the Lys residue in position 157 and the Lys residue in position 337 and the Asp residue in position 334 and the Ser residue in position 336 and the Val residue in position 158 and the Glu residue in position 296 and the Met residue in position 298 of SEQ ID NO:1 has(have) been replaced by another amino acid residue which can be encoded by nucleic acid constructs and, optionally, wherein one or more additional amino acid residue(s) in the remaining positions in the protease domain has been replaced by another amino acid residue which can be encoded by nucleic acid constructs; with the proviso that the variant is not FVII(Ala157), FVII(Ala334), FVII(Ala336), FVII(Ala337), FVII(Ala158), FVII(Ala296) or FVII(Ala298).

The term "FVII(Ala157)", as used herein means a coagulation factor VII variant with the sequence of SEQ ID NO:1, wherein the Lys at position 157 of SEQ ID NO:1 has been replaced by an alanine. This term does for example not include coagulation factor VII variants, wherein two or more amino acids at positions of SEQ ID NO:1 have been replaced by different amino acids.

The term "FVII(Ala337)", as used herein means a coagulation factor VII variant with the sequence of SEQ ID NO:1, wherein the Lys at position 337 of SEQ ID NO:1 has been replaced by an alanine. This term does for example not include coagulation factor VII variants, wherein two or more amino acids at positions of SEQ ID NO:1 have been replaced by different amino acids.

The term "FVII(Ala334)", as used herein means a coagulation factor VII variant with the sequence of SEQ ID NO:1, wherein the Asp at position 334 of SEQ ID NO:1 has been replaced by an alanine. This term does for example not include coagulation factor VII variants, wherein two or more amino acids at positions of SEQ ID NO:1 have been replaced by different amino acids.

The term "FVII(Ala336)", as used herein means a coagulation factor VII variant with the sequence of SEQ ID NO:1, wherein the Ser at position 336 of SEQ ID NO:1 has been replaced by an alanine. This term does for example not include coagulation factor VII variants, wherein two or more amino acids at positions of SEQ ID NO:1 have been replaced by different amino acids.

The term "FVII(Ala158)", as used herein means a coagulation factor VII variant with the sequence of SEQ ID NO:1, wherein the Val at position 158 of SEQ ID NO:1 has been replaced by an alanine. This term does for example not include coagulation factor VII variants, wherein two or more amino acids at positions of SEQ ID NO:1 have been replaced by different amino acids.

The term "FVII(Ala296)", as used herein means a coagulation factor VII variant with the sequence of SEQ ID NO:1, wherein the Glu at position 296 of SEQ ID NO:1 has been replaced by an alanine. This term does for example not include coagulation factor VII variants, wherein two or more amino acids at positions of SEQ ID NO:1 have been replaced by different amino acids.

The term "FVII(Ala298)", as used herein means a coagulation factor VII variant with the sequence of SEQ ID NO:1, wherein the Met at position 298 of SEQ ID NO:1 has been replaced by an alanine. This term does for example not include coagulation factor VII variants, wherein two or more amino acids at positions of SEQ ID NO:1 have been replaced by different amino acids.

In a further aspect, the invention relates to an isolated polynucleotide construct encoding a Factor VII polypeptide comprising at least two substitutions relative to the amino acid sequence of SEQ ID NO:l, wherein said substitutions are (i) replacement of L305 with any other amino acid, and (ii) replacement with any other amino acid of one or more amino acids selected from the group consisting of K157, K337, D334, S336, V158, E296, and M298.

In a further aspect, the invention provides a nucleic acid construct comprising a nucleotide sequence encoding a Factor VII variant.

In a further aspect, the invention provides a recombinant vector comprising the nucleic acid construct encoding a FVIIa variant.

In a further aspect, the invention provides a recombinant host cell comprising the nucleic acid construct or the vector.

In a further aspect, the invention provides a transgenic animal containing and expressing the nucleic acid construct.

In a further aspect, the invention provides a transgenic plant containing and expressing the nucleic acid construct.

In a further aspect, the invention relates to a method for producing the Factor VII polypeptide of the invention, the method comprising cultivating a cell comprising the nucleic acid construct in an appropriate growth medium under conditions allowing expression of the nucleic acid construct and recovering the resulting polypeptide from the culture medium.

In a further aspect, the invention provides a method for producing the Factor VII variant of the invention, the method comprising cultivating a cell comprising the nucleic acid construct in an appropriate growth medium under conditions allowing expression of the nucleic acid construct and recovering the resulting polypeptide from the culture medium.

In a further aspect, the invention relates to a method for producing the Factor VII polypeptide, the method comprising recovering the polypeptide from milk produced by the transgenic animal.

In a further aspect, the invention provides a method for producing the Factor VII variant, the method comprising recovering the variant from milk produced by the transgenic animal.

In a further aspect, the invention relates to a method for producing the Factor VII polypeptide, the method comprising cultivating a cell of a transgenic plant comprising the nucleic acid construct, and recovering the polypeptide from the resulting plant.

In a further aspect, the invention provides a method for producing the Factor VII variant, the method comprising cultivating a cell of a transgenic plant comprising the nucleic acid construct, and recovering the variant from the resulting plant.

In a further aspect, the invention relates to a pharmaceutical composition comprising a Factor VII polypeptide comprising the amino acid sequence of SEQ ID NO:1 or a variant thereof, wherein at least the amino acid corresponding to the Lys at position 157 of SEQ ID NO:1 has been replaced by a different amino acid; and, optionally, a pharmaceutically acceptable carrier.

In a further aspect, the invention relates to a pharmaceutical composition comprising a Factor VII polypeptide comprising the amino acid sequence of SEQ ID NO:1 or a variant thereof, wherein at least the amino acid corresponding to the Lys at position 337 of SEQ ID NO:1 has been replaced by a different amino acid; and, optionally, a pharmaceutically acceptable carrier.

In a further aspect, the invention relates to a pharmaceutical composition comprising a Factor VII polypeptide comprising the amino acid sequence of SEQ ID NO:1 or a variant thereof, wherein at least the amino acid corresponding to the Asp at position 334 of SEQ ID NO:1 has been replaced by a different amino acid; and, optionally, a pharmaceutically acceptable carrier.

In a further aspect, the invention relates to a pharmaceutical composition comprising a Factor VII polypeptide comprising the amino acid sequence of SEQ ID NO:1 or a variant thereof, wherein at least the amino acid corresponding to the Ser at position 336 of SEQ ID NO:1 has been replaced by a different amino acid; and, optionally, a pharmaceutically acceptable carrier.

In a further aspect, the invention relates to a pharmaceutical composition comprising a Factor VII polypeptide comprising the amino acid sequence of SEQ ID NO:1 or a variant thereof, wherein at least the amino acid corresponding to the Val at position 158 of SEQ ID NO:1 has been replaced by a different amino acid; and, optionally, a pharmaceutically acceptable carrier.

In a further aspect, the invention relates to a pharmaceutical composition comprising a Factor VII polypeptide comprising the amino acid sequence of SEQ ID NO:1 or a variant thereof, wherein at least the amino acid corresponding to the Glu at position 296 of SEQ ID NO:1 has been replaced by a different amino acid; and, optionally, a pharmaceutically acceptable carrier.

In a further aspect, the invention relates to a pharmaceutical composition comprising a Factor VII polypeptide comprising the amino acid sequence of SEQ ID NO:1 or a variant thereof, wherein at least the amino acid corresponding to the Met at position 298 of SEQ ID NO:1 has been replaced by a different amino acid; and, optionally, a pharmaceutically acceptable carrier.

In a further aspect, the invention provides a pharmaceutical composition comprising a coagulation Factor VII variant, wherein one or more of the Lys residue in position 157 and the Lys residue in position 337 and the Asp residue in position 334 and the Ser residue in position 336 and the Val residue in position 158 and the Glu residue in position 296 and the Met residue in position 298 of SEQ ID NO:1 has(have) been replaced by another amino acid residue which can be encoded by nucleic acid constructs and, optionally, wherein one or more additional amino acid residue(s) in the remaining positions in the protease domain has been replaced by another amino acid residue which can be encoded by nucleic acid constructs; and, optionally, a pharmaceutically acceptable carrier.

In a further aspect, the invention relates to the use of a Factor VII polypeptide comprising the amino acid sequence of SEQ ID NO:1 or a variant thereof, wherein at least the amino acid corresponding to the Lys at position 157 of SEQ ID NO:1 has been replaced by a different amino acid; for the preparation of a medicament for the treatment of bleeding episodes or for the enhancement of the normal haemostatic system.

In a further aspect, the invention relates to the use of a Factor VII polypeptide comprising the amino acid sequence of SEQ ID NO:1 or a variant thereof, wherein at least the amino acid corresponding to the Lys at position 337 of SEQ ID NO:1 has been replaced by a different amino acid; for the preparation of a medicament for the treatment of bleeding episodes or for the enhancement of the normal haemostatic system.

In a further aspect, the invention relates to the use of a Factor VII polypeptide comprising the amino acid sequence of SEQ ID NO:1 or a variant thereof, wherein at least the amino acid corresponding to the Asp at position 334 of SEQ ID NO:1 has been replaced by a different amino acid; for the preparation of a medicament for the treatment of bleeding episodes or for the enhancement of the normal haemostatic system.

In a further aspect, the invention relates to the use of a Factor VII polypeptide comprising the amino acid sequence of SEQ ID NO:1 or a variant thereof, wherein at least the amino acid corresponding to the Ser at position 336 of SEQ ID NO:1 has been replaced by a different amino acid; for the preparation of a medicament for the treatment of bleeding episodes or for the enhancement of the normal haemostatic system.

In a further aspect, the invention relates to the use of a Factor VII polypeptide comprising the amino acid sequence of SEQ ID NO:1 or a variant thereof, wherein at least the amino acid corresponding to the Val at position 158 of SEQ ID NO:1 has been replaced by a different amino acid; for the preparation of a medicament for the treatment of bleeding episodes or for the enhancement of the normal haemostatic system.

In a further aspect, the invention relates to the use of a Factor VII polypeptide comprising the amino acid sequence of SEQ ID NO:1 or a variant thereof, wherein at least the amino acid corresponding to the Glu at position 296 of SEQ ID NO:1 has been replaced by a different amino acid; for the preparation of a medicament for the treatment of bleeding episodes or for the enhancement of the normal haemostatic system.

In a further aspect, the invention relates to the use of a Factor VII polypeptide comprising the amino acid sequence of SEQ ID NO:1 or a variant thereof, wherein at least the amino acid corresponding to the Met at position 298 of SEQ ID NO:1 has been replaced by a different amino acid; for the preparation of a medicament for the treatment of bleeding episodes or for the enhancement of the normal haemostatic system.

In a further aspect, the invention provides the use of a coagulation Factor VII variant, wherein one or more of the Lys residue in position 157 and the Lys residue in position 337 and the Asp residue in position 334 and the Ser residue in position 336 and the Val residue in position 158 and the Glu residue in position 296 and the Met residue in position 298 of SEQ ID NO:1 has(have) been replaced by another amino acid residue which can be encoded by nucleic acid constructs and, optionally, wherein one or more additional amino acid residue(s) in the remaining positions in the protease domain has been replaced by another amino acid residue which can be encoded by nucleic acid constructs; for the preparation of a medicament for the treatment of bleeding episodes or for the enhancement of the normal haemostatic system.

In a further aspect, the invention relates to a method for the treatment of bleeding episodes in a subject or for the enhancement of the normal haemostatic system, the method comprising administering a therapeutically or prophylactically effective amount of a Factor VII polypeptide comprising the amino acid sequence of SEQ ID NO:1 or a variant thereof, wherein at least the amino acid corresponding to the Lys at position 157 of SEQ ID NO:1 has been replaced by a different amino acid; to a subject in need thereof.

In a further aspect, the invention relates to a method for the treatment of bleeding episodes in a subject or for the enhancement of the normal haemostatic system, the method comprising administering a therapeutically or prophylactically effective amount of a Factor VII polypeptide comprising the amino acid sequence of SEQ ID NO:1 or a variant thereof, wherein at least the amino acid corresponding to the Lys at position 337 of SEQ ID NO:1 has been replaced by a different amino acid; to a subject in need thereof.

In a further aspect, the invention relates to a method for the treatment of bleeding episodes in a subject or for the enhancement of the normal haemostatic system, the method comprising administering a therapeutically or prophylactically effective amount of a Factor VII polypeptide comprising the amino acid sequence of SEQ ID NO:1 or a variant thereof, wherein at least the amino acid corresponding to the Asp at position 334 of SEQ ID NO:1 has been replaced by a different amino acid; to a subject in need thereof.

In a further aspect, the invention relates to a method for the treatment of bleeding episodes in a subject or for the enhancement of the normal haemostatic system, the method comprising administering a therapeutically or prophylactically effective amount of a Factor VII polypeptide comprising the amino acid sequence of SEQ ID NO:1 or a variant thereof, wherein at least the amino acid corresponding to the Ser at position 336 of SEQ ID NO:1 has been replaced by a different amino acid; to a subject in need thereof.

In a further aspect, the invention relates to a method for the treatment of bleeding episodes in a subject or for the enhancement of the normal haemostatic system, the method comprising administering a therapeutically or prophylactically effective amount of a Factor VII polypeptide comprising the amino acid sequence of SEQ ID NO:1 or a variant thereof, wherein at least the amino acid corresponding to the Val at position 158 of SEQ ID NO:1 has been replaced by a different amino acid; to a subject in need thereof.

In a further aspect, the invention relates to a method for the treatment of bleeding episodes in a subject or for the enhancement of the normal haemostatic system, the method comprising administering a therapeutically or prophylactically effective amount of a Factor VII polypeptide comprising the amino acid sequence of SEQ ID NO:1 or a variant thereof, wherein at least the amino acid corresponding to the Glu at position 296 of SEQ ID NO:1 has been replaced by a different amino acid; to a subject in need thereof.

In a further aspect, the invention relates to a method for the treatment of bleeding episodes in a subject or for the enhancement of the normal haemostatic system, the method comprising administering a therapeutically or prophylactically effective amount of a Factor VII polypeptide comprising the amino acid sequence of SEQ ID NO:1 or a variant thereof, wherein at least the amino acid corresponding to the Met at position 298 of SEQ ID NO:1 has been replaced by a different amino acid; to a subject in need thereof.

In a further aspect, the invention provides a method for the treatment of bleeding episodes in a subject or for the enhancement of the normal haemostatic system, the method comprising administering a therapeutically or prophylactically effective amount of a coagulation Factor VII variant, wherein one or more of the Lys residue in position 157 and the Lys residue in position 337 and the Asp residue in position 334 and the Ser residue in position 336 and the Val residue in position 158 and the Glu residue in position 296 and the Met residue in position 298 of SEQ ID NO:1 has(have) been replaced by another amino acid residue which can be encoded by nucleic acid constructs and, optionally, wherein one or more additional amino acid residue(s) in the remaining positions in the protease domain has been replaced by another amino acid residue which can be encoded by nucleic acid constructs; to a subject in need thereof.

In a further aspect, the invention provides a pharmaceutical composition comprising a coagulation Factor VII variant, wherein one or more of the Lys residue in position 157 and the Lys residue in position 337 and the Asp residue in position 334 and the Ser residue in position 336 and the Val residue in position 158 and the Glu residue in position 296 and the Met residue in position 298 of SEQ ID NO:1 has(have) been replaced by another amino acid residue which can be encoded by nucleic acid constructs and, optionally, wherein one or more additional amino acid residue(s) in the remaining positions in the protease domain has been replaced by another amino acid residue which can be encoded by nucleic acid constructs; with the proviso that the variant is not FVII (Ala157), FVII(Ala334), FVII(Ala336), FVII(Ala337), FVII(Ala158), FVII(Ala296) or FVII(Ala298); and optionally, a pharmaceutically acceptable carrier.

In a further aspect, the invention provides the use of a coagulation Factor VII variant, wherein one or more of the Lys residue in position 157 and the Lys residue in position 337 and the Asp residue in position 334 and the Ser residue in position 336 and the Val residue in position 158 and the Glu residue in position 296 and the Met residue in position 298 of SEQ ID NO:1 has(have) been replaced by another amino acid residue which can be encoded by nucleic acid constructs and, optionally, wherein one or more additional amino acid residue(s) in the remaining positions in the protease domain has been replaced by another amino acid residue which can be encoded by nucleic acid constructs; with the proviso that the variant is not FVII(Ala157), FVII(Ala334), FVII(Ala336), FVII(Ala337), FVII(Ala158), FVII(Ala296) or FVII(Ala298); for the preparation of a medicament for the treatment of bleeding episodes or for the enhancement of the normal haemostatic system.

In a further aspect, the invention provides a method for the treatment or prophylaxis of bleeding disorders in a subject or for the enhancement of the normal haemostatic system, the method comprising administering a therapeutically or prophylactically effective amount of a coagulation Factor VII variant, wherein one or more of the Lys residue in position 157 and the Lys residue in position 337 and the Asp residue in position 334 and the Ser residue in position 336 and the Val residue in position 158 and the Glu residue in position 296 and the Met residue in position 298 of SEQ ID NO:1 has (have) been replaced by another amino acid residue which can be encoded by nucleic acid constructs and, optionally, wherein one or more additional amino acid residue(s) in the remaining positions in the protease domain has been replaced by another amino acid residue which can be encoded by nucleic acid constructs; with the proviso that the variant is not FVII(Ala157), FVII(Ala334), FVII(Ala336), FVII(Ala337), FVII(Ala158), FVII(Ala296) or FVII(Ala298); to a subject in need thereof.

In one embodiment of the invention, the factor VII polypeptide is a polypeptide, wherein the amino acid corresponding to the Lys at position 157 of SEQ ID NO:1 has been replaced by a different amino acid.

In a further embodiment of the invention, the factor VII polypeptide is a polypeptide, wherein the amino acid corresponding to the Lys at position 337 of SEQ ID NO:1 has been replaced by a different amino acid.

In a further embodiment of the invention, the factor VII polypeptide is a polypeptide, wherein the amino acid corresponding to the Asp at position 334 of SEQ ID NO:1 has been replaced by a different amino acid.

In a further embodiment of the invention, the factor VII polypeptide is a polypeptide, wherein the amino acid corresponding to the Ser at position 336 of SEQ ID NO:1 has been replaced by a different amino acid.

In a further embodiment of the invention, the factor VII polypeptide is a polypeptide, wherein the amino acid corresponding to the Val at position 158 of SEQ ID NO:1 has been replaced by a different amino acid.

In a further embodiment of the invention, the factor VII polypeptide is a polypeptide, wherein the amino acid corresponding to the Glu at position 296 of SEQ ID NO:1 has been replaced by a different amino acid.

In a further embodiment of the invention, the factor VII polypeptide is a polypeptide, wherein the amino acid corresponding to the Met at position 298 of SEQ ID NO:1 has been replaced by a different amino acid.

In a further embodiment of the invention, the factor VII polypeptide is a polypeptide, wherein at least one amino acid in the remaining positions in the protease domain has been replaced by a different amino acid.

In a further embodiment of the invention, the factor VII polypeptide is a polypeptide, wherein at the most 20 additional amino acids in the remaining positions in the protease domain have been replaced by different amino acids.

In a further embodiment of the invention, the factor VII polypeptide is a polypeptide, wherein at least one amino acid corresponding to an amino acid at a position selected from 159-170 of SEQ ID NO:1 has been replaced by a different amino acid.

In a further embodiment of the invention, the factor VII polypeptide is a polypeptide, wherein at least one amino acid corresponding to an amino acid at a position selected from 290-312 of SEQ ID NO:1 has been replaced by a different amino acid.

In a further embodiment of the invention, the factor VII polypeptide is a polypeptide, wherein at least one amino acid corresponding to an amino acid at a position selected from 330-339 of SEQ ID NO:1 has been replaced by a different amino acid.

In a further embodiment of the invention, the factor VII polypeptide is a polypeptide, wherein said Lys at position 157 of SEQ ID NO:1 has been replaced by an amino acid selected from the group consisting of Gly, Val, Ser, Thr, Asn, Gln, Asp, and Glu.

In a further embodiment of the invention, the factor VII polypeptide is a polypeptide, wherein said Lys at position 337 of SEQ ID NO:1 has been replaced by an amino acid selected from the group consisting of Ala, Gly, Val, Ser, Thr, Asn, Gln, Asp, and Glu.

In a further embodiment of the invention, the factor VII polypeptide is a polypeptide, wherein said Asp at position 334 of SEQ ID NO:1 has been replaced by an amino acid selected from the group consisting of Gly, and Glu.

In a further embodiment of the invention, the factor VII polypeptide is a polypeptide, wherein said Ser at position 336 of SEQ ID NO:1 has been replaced by an amino acid selected from the group consisting of Gly, and Glu.

In a further embodiment of the invention, the factor VII polypeptide is a polypeptide, wherein said Val at position 158 of SEQ ID NO:1 has been replaced by an amino acid selected from the group consisting of Ser, Thr, Asn, Gln, Asp, and Glu.

In a further embodiment of the invention, the factor VII polypeptide is a polypeptide, wherein said Glu at position 296 of SEQ ID NO:1 has been replaced by an amino acid selected from the group consisting of Arg, Lys, and Val.

In a further embodiment of the invention, the factor VII polypeptide is a polypeptide, wherein said Met at position 298 of SEQ ID NO:1 has been replaced by an amino acid selected from the group consisting of Lys, Arg, Gln, and Asn.

In a further embodiment of the invention, the factor VII polypeptide is a polypeptide, wherein the amino acid has been replaced by a different amino acid which can be encoded by nucleic acid constructs.

In a further embodiment of the invention, the factor VII polypeptide is a polypeptide, wherein said Factor VII polypeptide is human Factor VII.

In a further embodiment of the invention, the factor VII polypeptide is a polypeptide, wherein said Factor VII polypeptide is human Factor VIIa.

In a further embodiment of the invention, the factor VII polypeptide is a polypeptide independently selected from the group consisting of [E296V]-FVII, [M298Q]-FVII, and [S336G]-FVII.

In a further embodiment of the invention, the factor VII polypeptide is a polypeptide independently selected from the group consisting of [V158T/M298Q]-FVII, [E296V/M298Q]-FVII, [V158D/E296V]-FVII, [V158D/M298Q]-FVII, and [V158D/M298K]-FVII.

In a further embodiment of the invention, the factor VII polypeptide is [V158D/E296V/M298Q]-FVII.

In a further embodiment of the invention, the factor VII polypeptide is [V158D/E296V/M298Q/K337A]-FVII.

In a further embodiment, the factor VII variants are variants wherein one or more of the Lys residue in position 157 and the Lys residue in position 337 and the Asp residue in position 334 and the Ser residue in position 336 and the Val residue in position 158 and the Glu residue in position 296 and the Met residue in position 298 of SEQ ID NO:1 has(have) been replaced by another amino acid residue which can be encoded by nucleic acid constructs and, optionally, wherein one or more additional amino acid residue(s) in the remaining positions in the protease domain has been replaced by another amino acid residue which can be encoded by nucleic acid constructs;

with the proviso that the variant is not FVII(Ala157), FVII(Ala334), FVII(Ala336), FVII(Ala337), FVII(Ala158), FVII(Ala296) or FVII(Ala298).

In one embodiment, the factor VII variants are variants wherein one or more of the Lys residue in position 157 and the Lys residue in position 337 and the Asp residue in position 334 and the Ser residue in position 336 and the Val residue in position 158 and the Glu residue in position 296 and the Met residue in position 298 of SEQ ID NO:1 has(have) been replaced by another amino acid residue which can be encoded by nucleic acid constructs; with the proviso that the variant is not FVII(Ala157), FVII(Ala334), FVII(Ala336), FVII(Ala337), FVII(Ala158), FVII(Ala296) or FVII(Ala298).

In a further embodiment, one or more of the Lys residue in position 157 and the Lys residue in position 337 of SEQ ID NO:1 has(have) been replaced by another amino acid residue which can be encoded by nucleic acid constructs.

In a further embodiment, one or more of the Lys residue in position 157 and the Val residue in position 158 and the Glu residue in position 296 and the Met residue in position 298 of SEQ ID NO:1 has(have) been replaced by another amino acid residue which can be encoded by nucleic acid constructs.

In a further embodiment, the Lys residue in position 157 and one or more of the Val residue in position 158 and the Glu residue in position 296 and the Met residue in position 298 of SEQ ID NO:1 has(have) been replaced by another amino acid residue which can be encoded by nucleic acid constructs.

In a further embodiment, one or more of the Lys residue in position 157 and the Asp residue in position 334 and the Ser residue in position 336 of SEQ ID NO:1 has(have) been replaced by another amino acid residue which can be encoded by nucleic acid constructs.

In a further embodiment, the Lys residue in position 157 and one or more of the Asp residue in position 334 and the Ser residue in position 336 of SEQ ID NO:1 has(have) been replaced by another amino acid residue which can be encoded by nucleic acid constructs.

In a further embodiment, one or more of the Lys residue in position 337 and the Val residue in position 158 and the Glu residue in position 296 and the Met residue in position 298 of SEQ ID NO:1 has(have) been replaced by another amino acid residue which can be encoded by nucleic acid constructs.

In a further embodiment, the Lys residue in position 337 and one or more of the Val residue in position 158 and the Glu residue in position 296 and the Met residue in position 298 of SEQ ID NO:1 has(have) been replaced by another amino acid residue which can be encoded by nucleic acid constructs.

In a further embodiment, one or more of the Lys residue in position 337 and the Asp residue in position 334 and the Ser residue in position 336 of SEQ ID NO:1 has(have) been replaced by another amino acid residue which can be encoded by nucleic acid constructs.

In a further embodiment, the Lys residue in position 337 and one or more of the Asp residue in position 334 and the Ser residue in position 336 of SEQ ID NO:1 has(have) been replaced by another amino acid residue which can be encoded by nucleic acid constructs.

In a further embodiment, one or more of the Val residue in position 158 and the Glu residue in position 296 and the Met residue in position 298 and one or more of the Asp residue in position 334 and the Ser residue in position 336 of SEQ ID NO:1 has(have) been replaced by another amino acid residue which can be encoded by nucleic acid constructs.

In a further embodiment, the Lys residue in position 157 of SEQ ID NO:1 has(have) been replaced by another amino acid residue which can be encoded by nucleic acid constructs.

In a further embodiment, the Lys residue in position 337 of SEQ ID NO:1 has(have) been replaced by another amino acid residue which can be encoded by nucleic acid constructs.

In a further embodiment, one or more of the Val residue in position 158 and the Glu residue in position 296 and the Met residue in position 298 of SEQ ID NO:1 has(have) been replaced by another amino acid residue which can be encoded by nucleic acid constructs.

In a further embodiment, one or more of the Asp residue in position 334 and the Ser residue in position 336 of SEQ ID NO:1 has(have) been replaced by another amino acid residue which can be encoded by nucleic acid constructs.

In a further embodiment, the Lys residue in position 157 has been replaced by Gly, Val, Ser, Thr, Asn, Gln, Asp or Glu; and/or the Lys residue in position 337 has been replaced by Gly, Val, Ser, Thr, Asn, Gln, Asp or Glu; and/or the Val residue in position 158 has been replaced by Ser, Thr, Asn, Gln, Asp or Glu; and/or the Glu residue in position 296 has been replaced by Arg, Lys or Val; and/or the Met residue in position 298 has been replaced by Arg, Lys, Gln or Asn; and/or the Asp residue in position 334 has been replaced by Glu; and/or the Ser residue in position 336 has been replaced by Gly.

In a further embodiment the Lys residue in position 157 or the Lys residue in position 337 or the Asp residue in position 334 or the Ser residue in position 336 is the only amino acid residue that has been replaced.

In a further embodiment, the Val residue in position 158 and the Glu residue in position 296 and the Met residue in position 298 are the only amino acid residues that have been replaced.

In a further embodiment, the ratio between the activity of a variant according to the invention and the activity of the native Factor VII polypeptide shown in SEQ ID NO:1 is at least about 1.25 when tested in the "In Vitro Hydrolysis Assay" defined herein. In another embodiment, the ratio is at least about 2.0; in another embodiment, at least about 4.0.

In a further embodiment, the Gln residue in position 312 in the protease domain has not been replaced.

In a further embodiment, the recombinant host cell is of mammalian origin. In another embodiment, the cell is selected from the group consisting of CHO cells, BHK cells or HEK cells.

In a further embodiment, at the most 20 additional amino acid residues in the remaining positions in the protease domain (positions 153-406) have been replaced. In one embodiment, at the most 15 additional amino acid residues are replaced; in another embodiment, at the most 10 amino acid residues are replaced; in another embodiment, at the most 5 amino acid residues are replaced.

In a further embodiment, one or more of the amino acid residues in positions 157, 337, 158, 296, 298, 334, or 336 is/are the only amino acid residue(s) that has/have been replaced.

In a further embodiment, one or both of the Lys residues in position 157 and in position 337 has/have been replaced by a neutral amino acid residue, or one of the residues has been replaced by a negatively charged amino acid residue, or one Lys residue has been replaced by a neutral amino acid residue and one Lys residue has been replaced by a negatively charged amino acid residue.

In a further embodiment, one or both of the Asp residue in position 334 and the Ser residue in position 336 has/have been replaced by an amino acid residue that is able to form hydrogen bonds and/or able to form a salt bridge, or one or both of the residues is/are replaced by a small amino acid residue.

In a further embodiment, the Lys residue in position 157 and/or the Lys residue in position 337 is/are the only amino acid residue(s) that has/have been replaced. In one embodiment, the Lys residue in position 157 has been replaced. In another embodiment, the Lys residue in position 337 has been replaced.

In a further embodiment, the Val residue in position 158 and/or the Met residue in position 298 is/are the only amino acid residue(s) that has/have been replaced.

In a further embodiment, the Asp residue in position 334 and/or the Ser residue in position 336 is/are the only amino acid residue(s) that has/have been replaced.

In a further embodiment, the Lys residue at position 157 has been replaced by an amino acid residue selected from a list of Val, Leu, Ile, Met, Phe, Trp, Pro, Gly, Ser, Thr, Cys, Tyr, Asn, Glu, Arg, His, Asp, and Gln. In another embodiment, the Lys residue in position 157 has been replaced by an amino acid residue selected from the group consisting of Gly, Val, Ser, Thr, Asn, Gln, Asp, and Glu.

In a further embodiment, Lys residue at position 337 has been replaced by an amino acid residue selected from a list of Val, Leu, Ile, Met, Phe, Trp, Pro, Gly, Ser, Thr, Cys, Tyr, Asn, Glu, Arg, His, Asp or Gln. In another embodiment, the Lys residue in position 337 has been replaced by Gly, Val, Ser, Thr, Asn, Gln, Asp or Glu.

In a further embodiment, Val residue in position 158 has been replaced by an amino acid residue selected from a list of Leu, Ile, Met, Phe, Trp, Pro, Gly, Ser, Thr, Cys, Tyr, Asn, Glu, Lys, Arg, His, Asp and Gln. In a further embodiment, the Val residue in position 158 has been replaced by an amino acid residue selected from the group consisting of Ser, Thr, Asn, Gln, Asp and Glu.

In a further embodiment, the Glu residue in position 296 has been replaced by an amino acid residue selected from a list of Val, Leu, Ile, Met, Phe, Trp, Pro, Gly, Ser, Thr, Cys, Tyr, Asn, Lys, Arg, His, Asp or Gln. In a further embodiment, the residue has been replaced by Arg, Lys or Val.

In a further embodiment, the Met residue in position 298 has been replaced by an amino acid residue selected from a list of Val, Leu, Ile, Phe, Trp, Pro, Gly, Ser, Thr, Cys, Tyr, Asn, Lys, Arg, His, Glu, Asp or Gln. In another embodiment, the residue has been replaced by Lys, Arg, Gln or Asn.

In a further embodiment, the Asp residue in position 334 has been replaced by Gly and Glu.

In a further embodiment, the Ser residue in position 336 that has been replaced by Gly and Glu.

In a further embodiment of the invention the ratio between the activity of the variant and the activity of the native Factor VII polypeptide shown in SEQ ID NO:1 is at least about 1.25 when tested in the "In Vitro Hydrolysis Assay" as defined herein (Example 11). In another embodiment, the ratio is at least about 2.0; in yet another embodiment, at least about 4.0.

In a further aspect, the invention provides FVIIa variants that have increased tissue factor-independent activity compared to native FVIIa. In one embodiment thereof, the increased activity is not accompanied by changes in the substrate specificity. In one embodiment, the binding of the variants to tissue factor are not impaired (compared to wild-type FVIIa); in another embodiment, the variants have at least the activity of wild-type Factor VIIa when bound to tissue factor.

In a further embodiment, the Factor VII variants, in addition to the already performed amino acid replacement in positions 157, 158, 296, 298, 334, 336 or 337 and the optional amino acid replacements elsewhere in the protease domain, also have some amino acid residues replaced in the N-terminal Gla domain (residues 1-37). In one embodiment, one or more of the amino acid residues in positions 10 and 32 (referring to SEQ ID NO:1) of Factor VII is/are replaced with another amino acid residue that can be encoded by nucleic acid constructs. In one embodiment, the amino acid residue Pro in position 10 is replaced by Gln, Arg, His, Gln, Asn or Lys; and/or the amino acid residue Lys in position 32 is replaced by Glu, Gln or Asn.

BRIEF DESCRIPTION OF THE DRAWINGS

FIG. 1 shows the full amino acid sequence of native human coagulation Factor VII (SEQ ID NO:1).

In the present specification, amino acids are represented using abbreviations, as indicated in table 1, approved by IUPAC-IUB Commission on Biochemical Nomenclature (CBN). Amino acid and the like having isomers represented by name or the following abbreviations are in natural L-form unless otherwise indicated. Further, the left and right ends of an amino acid sequence of a peptide are, respectively, the N- and C-termini unless otherwise specified.

TABLE 1

Abbreviations for amino acids:

| Amino acid | Tree-letter code | One-letter code |
|---|---|---|
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

It has now been found that FVIIa variants wherein at least one of the amino acid residues Lys157, Val158, Glu296, Met298, Asp334, Ser336 or Lys337 (and optionally one or more additional residues) is/are replaced by another amino acid residue having coagulant activity, preferably substituted with an amino acid other than Ala.

The residues are located in an area believed to affect the insertion of the amino terminus of the protease domain and thereby the formation of the catalytically active conformation of Factor VIIa which is dependent on a salt bridge between the terminal amino group of Ile 153 and the side chain of Asp343. The replacements may remove electrostatic repulsions, add hydrogen bonds or otherwise facilitate the insertion of the amino terminus.

Due to the higher inherent activity of the described Factor VIIa variant compared to native FVIIa, a lower dose is foreseen to be adequate to obtain a functionally adequate concentration at the site of action and thus it will be possible to administer a lower dose to the subject having bleeding episodes or needing enhancement of the normal haemostatic system.

As discussed briefly above, it is hypothesized by the present inventors that by replacing one or more of the Lys residue in position 157 and the Lys residue in position 337 and the Val residue in position 158 and the Glu residue in position 296 and the Met residue in position 298 and the Asp residue in position 334 and the Ser residue in position 336, Factor VIIa will spontaneously attain a more active conformation that normally has to be induced by tissue factor. Such Factor VIIa variants exhibit an inherent activity which may be therapeutically useful in situations where the procoagulant activity is independent of tissue factor (Factor Xa generation on the platelet surface) such as for example, when high doses of NovoSeven® are administered.

Replacement of additional amino acid residues in the protease domain may, in addition to the effect obtained by replacement of one or more of the Lys residue in position 157 and the Lys residue in position 337 and the Val residue in position 158 and the Glu residue in position 296 and the Met residue in position 298 and the Asp residue in position 334 and the Ser residue in position 336, further facilitate formation of the active conformation of the molecule. It is believed, however, that the most pronounced effects will be seen when the above-mentioned mutations are carried out in the vicinity (sequential or three-dimensional) of these seven residues.

Replacement of a few amino acid residues in the N-terminal Gla domain (residues 1-37) of Factor VII may provide the protein with a substantially higher affinity for membrane phospholipids, such as membrane phospholipids of tissue factor-bearing cells or of platelets. Thus, the Factor VII variants mentioned above may, in addition to the already performed amino acid replacement in positions 157, 158, 296, 298, 334, 336 or 337 and the optional amino acid replacements elsewhere in the protease domain, also have some amino acid residues replaced in the N-terminal Gla domain, thereby obtaining a protein having an increased activity as well as an increased affinity for membrane phospholipids compared to native Factor VII. Preferably the amino acid residues in positions 10 and 32 (referring to SEQ ID NO:1) of Factor VII may be replaced with another amino acid residue that can be encoded by nucleic acid constructs. Examples of preferred amino acid residues to be incorporated in the above-mentioned positions are: The amino acid residue Pro in position 10 is replaced by Gln, Arg, His, Gln, Asn or Lys; and/or the amino acid residue Lys in position 32 is replaced by Glu, Gln or Asn.

Other residues in the Gla domain, based on the different phospholipid affinities and sequences of the vitamin K-dependent plasma proteins, may also be considered for substitution. In the present context the three-letter indications of the amino acids have been used in their conventional meaning. Unless indicated explicitly, the amino acids mentioned herein are L-amino acids.

The term "N-terminal GLA-domain" means the amino acid sequence 1-37 of FVII.

The term "protease domain" means the amino acid sequence 153-406 of FVII (the heavy chain of FVIIa).

The three-letter indication "GLA" means 4-carboxy-glutamic acid (γ-carboxyglutamate).

The term "neutral amino acid residue" (at pH 6-8) is intended to comprise amino acids selected from the list of Ala, Val, Leu, Ile, Pro, Met, Phe, Trp, Gly, Ser, Thr, Cys, Tyr, Asn, Gln.

The term "small amino acid" is intended to comprise amino acids selected from Gly, Glu and Ala.

The term "negatively charged amino acid residue" (at pH 6-8) is intended to comprise amino acids selected from Asp and Glu.

The term "Factor VII polypeptide" as used herein means any protein comprising the amino acid sequence 1-406 of native human Factor VII (SEQ ID NO:1) or variants thereof. This includes but are not limited to human Factor VII, human Factor VIIa and variants thereof.

The term "Factor VII" as used herein is intended to comprise the inactive one-chain zymogen Factor VII molecule as well as the activated two-chain Factor VII molecule (Factor VIIa). This includes proteins that have the amino acid sequence 1-406 of native human Factor VII or Factor VIIa. It also includes proteins with a slightly modified amino acid sequence, for instance, a modified N-terminal end including N-terminal amino acid deletions or additions so long as those proteins substantially retain the activity of Factor VIIa. The term "factor VIIa", or "FVIIa" as used herein means a product consisting of the activated form (factor VIIa). "Factor VII" or "Factor VIIa" within the above definition also includes natural allelic variations that may exist and occur from one individual to another. Also, degree and location of glycosylation or other post-translation modifications may vary depending on the chosen host cells and the nature of the host cellular environment.

The terms "variant" or "variants", as used herein, is intended to designate Factor VII having the sequence of SEQ ID NO:1, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein. Such addition can take place either at the N-terminal end or at the C-terminal end of the parent protein or both. The "variant" or "variants" within this definition have FVII activity in its activated two-chain molecular form. In one embodiment a variant is 65% identical with the sequence of SEQ ID NO:1. In one embodiment a variant is 80% identical with the sequence of SEQ ID NO:1. In another embodiment a variant is 90% identical with the sequence of SEQ ID NO:1. In a further embodiment a variant is 95% identical with the sequence of SEQ ID NO:1.

As used herein the term "nucleic acid construct" is intended to mean any nucleic acid molecule of cDNA, genomic DNA, synthetic DNA, semi synthetic DNA, RNA origin or mixed origin. The term "construct" is intended to indicate a nucleic acid segment which may be single- or double-stranded, and which may be based on a complete or partial naturally occurring nucleotide sequence encoding the polypeptide of interest. The construct may optionally contain other nucleic acid segments. In a similar way, the term "amino acid residue which can be encoded by nucleic acid constructs" covers amino acid residues which can be encoded by the nucleic acid constructs defined above, i.e. amino acids such as Ala, Val, Leu, Ile, Met, Phe, Trp, Pro, Gly, Ser, Thr, Cys, Tyr, Asn, Glu, Lys, Arg, His, Asp and Gln.

The term "a different amino acid" as used herein means an amino acid that are different from the amino acid naturally present at that position. This includes but are not limited to amino acids that can be encoded by a nucleic acid construct. Preferably the different amino acid is in natural L-form and can be encoded by a nucleic acid construct. A specific example being L-cysteine (Cys).

In the present context, the term "treatment" is meant to include both prevention of an expected bleeding, such as in surgery, and regulation of an already occurring bleeding, such as in trauma, with the purpose of inhibiting or minimising the bleeding. Prophylactic administration of the Factor VIIa variant according to the invention is thus included in the term "treatment".

The term "activity" as used herein means the ability of a Factor VII polypeptide or a variant thereof to convert its substrate Factor X to the active Factor Xa. The activity of a Factor VII polypeptide may be measured with the "In Vitro Proteolysis Assay".

The term "inherent activity" also includes the ability to generate thrombin on the surface of activated platelets in the absence of tissue factor.

The term "enhancement of the normal haemostatic system" means an enhancement of the ability to generate thrombin.

As used herein the term "bleeding disorder" reflects any defect, congenital, acquired or induced, of cellular or molecular origin that is manifested in bleedings. Examples are clotting factor deficiencies (e.g. haemophilia A and B or deficiency of coagulation Factors XI or VII), clotting factor inhibitors, defective platelet function, thrombocytopenia or von Willebrand's disease.

The term "bleeding episodes" is meant to include uncontrolled and excessive bleeding which is a major problem both in connection with surgery and other forms of tissue damage. Uncontrolled and excessive bleeding may occur in subjects having a normal coagulation system and subjects having coagulation or bleeding disorders. Clotting factor deficiencies (haemophilia A and B, deficiency of coagulation factors XI or VII) or clotting factor inhibitors may be the cause of bleeding disorders. Excessive bleedings also occur in subjects with a normally functioning blood clotting cascade (no clotting factor deficiencies or inhibitors against any of the coagulation factors) and may be caused by a defective platelet function, thrombocytopenia or von Willebrand's disease. In such cases, the bleedings may be likened to those bleedings caused by haemophilia because the haemostatic system, as in haemophilia, lacks or has abnormal essential clotting "compounds" (such as platelets or von Willebrand factor protein) that causes major bleedings. In subjects who experience extensive tissue damage in association with surgery or vast trauma, the normal haemostatic mechanism may be overwhelmed by the demand of immediate haemostasis and they may develop bleeding in spite of a normal haemostatic mechanism. Achieving satisfactory haemostasis also is a problem when bleedings occur in organs such as the brain, inner ear region and eyes with limited possibility for surgical haemostasis. The same problem may arise in the process of taking biopsies from various organs (liver, lung, tumour tissue, gastrointestinal tract) as well as in laparoscopic surgery. Common for all these situations is the difficulty to provide haemostasis by surgical techniques (sutures, clips, etc.) which also is the case when bleeding is diffuse (haemorrhagic gastritis and profuse uterine bleeding). Acute and profuse bleedings may also occur in subjects on anticoagulant therapy in whom a defective haemostasis has been induced by the therapy given. Such subjects may need surgical interventions in case the anticoagulant effect has to be counteracted rapidly. Radical retropubic prostatectomy is a commonly performed procedure for subjects with localized prostate cancer. The operation is frequently complicated by sigrnificant and sometimes massive blood loss. The considerable blood loss during prostatectomy is mainly related to the complicated anatomical situation, with various densely vascularized sites that are not easily accessible for surgical haemostasis, and which may result in diffuse bleeding from a large area. Another situation that may cause problems in the case of unsatisfactory haemostasis is when subjects with a normal haemostatic mechanism are given anticoagulant therapy to prevent thromboembolic disease. Such therapy may include heparin, other forms of proteoglycans, warfarin or other forms of vitamin K-antagonists as well as aspirin and other platelet aggregation inhibitors.

In one embodiment of the invention, the bleeding is associated with haemophilia. In another embodiment, the bleeding is associated with haemophilia with aquired inhibitors. In another embodiment, the bleeding is associated with thrombocytopenia. In another embodiment, the bleeding is associated with von Willebrand's disease. In another embodiment, the bleeding is associated with severe tissue damage. In another embodiment, the bleeding is associated with severe trauma. In another embodiment, the bleeding is associated with surgery. In another embodiment, the bleeding is associated with laparoscopic surgery. In another embodiment, the bleeding is associated with haemorrhagic gastritis. In another embodiment, the bleeding is profuse uterine bleeding. In another embodiment, the bleeding is occurring in organs with a limited possibility for mechanical haemostasis. In another embodiment, the bleeding is occurring in the brain, inner ear region or eyes. In another embodiment, the bleeding is associated with the process of taking biopsies. In another embodiment, the bleeding is associated with anticoagulant therapy.

The term "subject" as used herein is intended to mean any animal, in particular mammals, such as humans, and may, where appropriate, be used interchangeably with the term "patient".

As used herein the term "appropriate growth medium" means a medium containing nutrients and other components required for the growth of cells and the expression of the nucleic acid sequence encoding the Factor VII variant of the invention.

Preparation of Factor VII Variants

The Factor VII variants described herein may be produced by means of recombinant nucleic acid techniques. In general, a cloned wild-type Factor VII nucleic acid sequence is modified to encode the desired protein. This modified sequence is then inserted into an expression vector, which is in turn transformed or transfected into host cells. Higher eukaryotic cells, in particular cultured mammalian cells, are preferred as host cells. The complete nucleotide and amino acid sequences for human Factor VII are known (see U.S. Pat. No. 4,784,950, where the cloning and expression of recombinant human Factor VII is described). The bovine Factor VII sequence is described in Takeya et al., *J. Biol. Chem.* 263:14868-14872 (1988)).

The amino acid sequence alterations may be accomplished by a variety of techniques. Modification of the nucleic acid sequence may be by site-specific mutagenesis. Techniques for site-specific mutagenesis are well known in the art and are described in, for example, Zoller and Smith (*DNA* 3:479-488, 1984) or "Splicing by extension overlap", Horton et al., *Gene* 77, 1989, pp. 61-68. Thus, using the nucleotide and amino acid sequences of Factor VII, one may introduce the alteration(s) of choice. Likewise, procedures for preparing a DNA construct using polymerase chain reaction using specific primers are well known to persons skilled in the art (cf. *PCR Protocols,* 1990, Academic Press, San Diego, Calif., USA).

The nucleic acid construct encoding the Factor VII variant of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., *Molecular Cloning: A Laboratory Manual,* 2nd. Ed. Cold Spring Harbor Laboratory, Cold Spring Harbor, N.Y., 1989).

The nucleic acid construct encoding the Factor VII variant may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. According to the phosphoamidite method, oligonucleotides are synthesised, e.g. in an automatic DNA synthesiser, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct is preferably a DNA construct,

DNA sequences for use in producing Factor VII variants according to the present invention will typically encode a pre-pro polypeptide at the amino-terminus of Factor VII to obtain proper posttranslational processing (e.g. gamma-carboxylation of glutamic acid residues) and secretion from the host cell. The pre-pro polypeptide may be that of Factor VII or another vitamin K-dependent plasma protein, such as Factor IX, Factor X, prothrombin, protein C or protein S. As will be appreciated by those skilled in the art, additional modifications can be made in the amino acid sequence of the Factor VII variants where those modifications do not significantly impair the ability of the protein to act as a coagulant. For example, the Factor VII variants can also be modified in the activation cleavage site to inhibit the conversion of zymogen Factor VII into its activated two-chain form, as generally described in U.S. Pat. No. 5,288,629.

Expression vectors for use in expressing Factor VIIa variants will comprise a promoter capable of directing the transcription of a cloned gene or cDNA. Preferred promoters for use in cultured mammalian cells include viral promoters and cellular promoters. Viral promoters include the SV40 promoter (Subramani et al., *Mol. Cell. Biol.* 1:854-864, 1981) and the CMV promoter (Boshart et al., *Cell* 41:521-530, 1985). A particularly preferred viral promoter is the major late promoter from adenovirus 2 (Kaufman and Sharp, *Mol. Cell. Biol.* 2:1304-1319, 1982). Cellular promoters include the mouse kappa gene promoter (Bergman et al., *Proc. Natl. Acad. Sci. USA* 81:7041-7045, 1983) and the mouse $V_H$ promoter (Loh et al., *Cell* 33:85-93, 1983). A particularly preferred cellular promoter is the mouse metallothionein-1 promoter (Palmiter et al., *Science* 222:809-814, 1983). Expression vectors may also contain a set of RNA splice sites located downstream from the promoter and upstream from the insertion site for the Factor VII sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region, the human growth hormone gene terminator (DeNoto et al. *Nucl. Acids Res.* 9:3719-3730, 1981) or the polyadenylation signal from the human Factor VII gene or the bovine Factor VII gene. The expression vectors may also include a noncoding viral leader sequence, such as the adenovirus 2 tripartite leader, located between the promoter and the RNA splice sites; and enhancer sequences, such as the SV40 enhancer.

Cloned DNA sequences are introduced into cultured mammalian cells by, for example, calcium phosphate-mediated transfection (Wigler et al., *Cell* 14:725-732, 1978; Corsaro and Pearson, *Somatic Cell Genetics* 7:603-616, 1981; Graham and Van der Eb, *Virology* 52d:456-467, 1973) or electroporation (Neumann et al., *EMBO J.* 1:841-845, 1982). To identify and select cells that express the exogenous DNA, a gene that confers a selectable phenotype (a selectable marker) is generally introduced into cells along with the gene or cDNA of interest. Preferred selectable markers include genes that confer resistance to drugs such as neomycin, hygromycin, and methotrexate. The selectable marker may be an amplifiable selectable marker. A preferred amplifiable selectable marker is a dihydrofolate reductase (DHFR) sequence. Selectable markers are reviewed by Thilly (*Mammalian Cell Technology*, Butterworth Publishers, Stoneham, Mass., incorporated herein by reference). The person skilled in the art will easily be able to choose suitable selectable markers.

Selectable markers may be introduced into the cell on a separate plasmid at the same time as the gene of interest, or they may be introduced on the same plasmid. If, on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically for 1-2 days, to begin expressing the gene of interest. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The media are prepared using procedures known in the art (see, e.g., references for bacteria and yeast; Bennett, J. W. and LaSure, L., editors, *More Gene Manipulations in Fungi*, Academic Press, CA, 1991). Growth media generally include a carbon source, a nitrogen source, essential amino acids, essential sugars, vitamins, salts, phospholipids, proteins and growth factors. For production of gamma-carboxylated Factor VII variants, the medium will contain vitamin K, preferably at a concentration of about 0.1 mg/ml to about 5 mg/ml. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby increasing expression levels.

Clones of stably transfected cells are then screened for expression of the desired Factor VII variant.

Preferred mammalian cell lines include the CHO (ATCC CCL 61), COS-1 (ATCC CRL 1650), baby hamster kidney (BHK) and 293 (ATCC CRL 1573; Graham et al., *J. Gen. Virol.* 36:59-72, 1977) cell lines. A preferred BHK cell line is the tk⁻ ts13 BHK cell line (Waechter and Baserga, *Proc. Natl. Acad. Sci. USA* 79:1106-1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk⁻ ts13 BHK cell line is also available from the ATCC under accession number CRL 1632. In addition, a number of other cell lines may be used, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1) and DUKX cells (Urlaub and Chasin, *Proc. Natl. Acad. Sci. USA* 77:4216-4220, 1980).

Transgenic animal technology may be employed to produce the Factor VII variants of the invention. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and biochemically well characterized. Furthermore, the major milk proteins are present in milk at high concentrations (typically from about 1 to 15 g/l).

From a commercial point of view, it is clearly preferable to use as the host a species that has a large milk yield. While smaller animals such as mice and rats can be used (and are preferred at the proof of principle stage), it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk (see, for example, WO 88/00239 for a comparison of factors influencing the choice of host species). It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489), beta-lactoglobulin, a-lactalbumin, and whey acidic protein. The beta-lactoglobulin (BLG) promoter is preferred. In the case of the ovine beta-lactoglobulin gene, a region of at least the proximal 406 bp of 5' flanking sequence of the gene will generally be used, although larger portions of the 5' flanking sequence, up to about 5 kbp, are preferred, such as a ~4.25 kbp DNA segment encompassing the 5' flanking promoter and non-coding portion of the beta-lactoglobulin gene (see Whitelaw et al., *Biochem. J.* 286: 31-39 (1992)). Similar fragments of promoter DNA from other species are also suitable.

Other regions of the beta-lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., *Proc. Natl. Acad. Sci. USA* 85: 836-840 (1988); Palmiter et al., *Proc. Natl. Acad. Sci. USA* 88: 478-482 (1991); Whitelaw et al., *Transgenic Res.* 1: 3-13 (1991); WO 89/01343; and WO 91/02318, each of which is incorporated herein by reference). In this regard, it is generally preferred, where possible, to use genomic sequences containing all or some of the native introns of a gene encoding the protein or polypeptide of interest, thus the further inclusion of at least some introns from, e.g, the beta-lactoglobulin gene, is preferred. One such region is a DNA segment that provides for intron splicing and RNA polyadenylation from the 3' non-coding region of the ovine beta-lactoglobulin gene. When substituted for the natural 3' non-coding sequences of a gene, this ovine beta-lactoglobulin segment can both enhance and stabilize expression levels of the protein or polypeptide of interest. Within other embodiments, the region surrounding the initiation ATG of the variant Factor VII sequence is replaced with corresponding sequences from a milk specific protein gene. Such replacement provides a putative tissue-specific initiation environment to enhance expression. It is convenient to replace the entire variant Factor VII pre-pro and 5' non-coding sequences with those of, for example, the BLG gene, although smaller regions may be replaced.

For expression of Factor VII variants in transgenic animals, a DNA segment encoding variant Factor VII is operably linked to additional DNA segments required for its expression to produce expression units. Such additional segments include the above-mentioned promoter, as well as sequences that provide for termination of transcription and polyadenylation of mRNA. The expression units will further include a DNA segment encoding a secretory signal sequence operably linked to the segment encoding modified Factor VII. The secretory signal sequence may be a native Factor VII secretory signal sequence or may be that of another protein, such as a milk protein (see, for example, von Heijne, *Nucl. Acids Res.* 14: 4683-4690 (1986); and Meade et al., U.S. Pat. No. 4,873, 316, which are incorporated herein by reference).

Construction of expression units for use in transgenic animals is conveniently carried out by inserting a variant Factor VII sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of a variant Factor VII polypeptide; thereby creating a gene fusion that includes the expression control sequences of the milk protein gene. In any event, cloning of the expression units in plasmids or other vectors facilitates the amplification of the variant Factor VII sequence. Amplification is conveniently carried out in bacterial (e.g. *E. coli*) host cells, thus the vectors will typically include an origin of replication and a selectable marker functional in bacterial host cells. The expression unit is then introduced into fertilized eggs (including early-stage embryos) of the chosen host species. Introduction of heterologous DNA can be accomplished by one of several routes, including microinjection (e.g. U.S. Pat. No. 4,873,191), retroviral infection (Jaenisch, *Science* 240: 1468-1474 (1988)) or site-directed integration using embryonic stem (ES) cells (reviewed by Bradley et al., *Bio/Technology* 10: 534-539 (1992)). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds. General procedures for producing transgenic animals are known in the art (see, for example, Hogan et al., Manipulating the Mouse Embryo: A Laboratory Manual, Cold Spring Harbor Laboratory, 1986; Simons et al., *Bio/Technology* 6: 179-183 (1988); Wall et al., *Biol. Reprod.* 32: 645-651 (1985); Buhler et al., *Bio/Technology* 8: 140-143 (1990); Ebert et al., *Bio/*

Technology 9: 835-838 (1991); Krimpenfort et al., Bio/Technology 9: 844-847 (1991); Wall et al., J. Cell. Biochem. 49: 113-120 (1992); U.S. Pat. No. 4,873,191; U.S. Pat. No. 4,873,316; WO 88/00239, WO 90/05188, WO 92/11757; and GB 87/00458). Techniques for introducing foreign DNA sequences into mammals and their germ cells were originally developed in the mouse (see, e.g., Gordon et al., Proc. Natl. Acad. Sci. USA 77: 7380-7384 (1980); Gordon and Ruddle, Science 214: 1244-1246 (1981); Palmiter and Brinster, Cell 41: 343-345 (1985); Brinster et al., Proc. Natl. Acad. Sci. USA 82: 4438-4442 (1985); and Hogan et al. (ibid.)). These techniques were subsequently adapted for use with larger animals, including livestock species (see, e.g., WO 88/00239, WO 90/05188, and WO 92/11757; and Simons et al., Bio/Technology 6: 179-183 (1988)). To summarise, in the most efficient route used to date in the generation of transgenic mice or livestock, several hundred linear molecules of the DNA of interest are injected into one of the pro-nuclei of a fertilized egg according to established techniques. Injection of DNA into the cytoplasm of a zygote can also be employed.

Production in transgenic plants may also be employed. Expression may be generalised or directed to a particular organ, such as a tuber (see, Hiatt, Nature 344:469-479 (1990); Edelbaum et al., J. Interferon Res. 12:449-453 (1992); Sijmons et al., Bio/Technology 8:217-221 (1990); and EP 0 255 378).

The Factor VII variants of the invention are recovered from cell culture medium or milk. The Factor VII variants of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989). Preferably, they may be purified by affinity chromatography on an anti-Factor VII antibody column. The use of calcium-dependent monoclonal antibodies, as described by Wakabayashi et al., J. Biol. Chem. 261:11097-11108, (1986) and Thim et al., Biochemistry 27: 7785-7793, (1988), is particularly preferred. Additional purification may be achieved by conventional chemical purification means, such as high performance liquid chromatography. Other methods of purification, including barium citrate precipitation, are known in the art, and may be applied to the purification of the novel Factor VII variants described herein (see, for example, Scopes, R., Protein Purification, Springer-Verlag, N.Y., 1982).

For therapeutic purposes it is preferred that the Factor VII variants of the invention are substantially pure. Thus, in a preferred embodiment of the invention the Factor VII variants of the invention is purified to at least about 90 to 95% homogeneity, preferably to at least about 98% homogeneity. Purity may be assessed by e.g. gel electrophoresis and amino-terminal amino acid sequencing.

The Factor VII variant is cleaved at its activation site in order to convert it to its two-chain form. Activation may be carried out according to procedures known in the art, such as those disclosed by Osterud, et al., Biochemistry 11:2853-2857 (1972); Thomas, U.S. Pat. No. 4,456,591; Hedner and Kisiel, J. Clin. Invest. 71:1836-1841 (1983); or Kisiel and Fujikawa, Behring Inst. Mitt. 73:29-42 (1983). Alternatively, as described by Bjoern et al. (Research Disclosure, 269 September 1986, pp. 564-565), Factor VII may be activated by passing it through an ion-exchange chromatography column, such as Mono Q® (Pharmacia fine Chemicals) or the like. The resulting activated Factor VII variant may then be formulated and administered as described below.

Assays

The invention also provides suitable assays for selecting preferred Factor VIIa variants according to the invention. These assays can be performed as a simple preliminary in vitro test.

Thus, Example 11 herein discloses a simple test (entitled "In Vitro Hydrolysis Assay") for the activity of Factor VIIa variants of the invention. Based thereon, Factor VIIa variants which are of particular interest are such variants where the ratio between the activity of the variant and the activity of native Factor VII shown in FIG. 1 is above 1.0, e.g. at least about 1.25, preferably at least about 2.0, such as at least about 3.0 or, even more preferred, at least about 4.0 when tested in the "In Vitro Hydrolysis Assay" defined herein.

The activity of the variants can also be measured using a physiological substrate such as factor X (In Vitro Proteolysis Assay, see Example 12), suitably at a concentration of 100-1000 nM, where the factor Xa generated is measured after the addition of a suitable chromogenic substrate (eg. S-2765). In addition, the activity assay may be run at physiological temperature.

The ability of the FVIIa variants to generate thrombin can also be measured in an assay comprising all relevant coagulation factors and inhibitors at physiological concentrations (minus factor VIII when mimicking hemophilia A conditions) and activated platelets (as described on p. 543 in Monroe et al. (1997) Brit. J. Haematol. 99, 542-547 which is hereby incorporated as reference).

Administration and Pharmaceutical Compositions

The Factor VII variants according to the present invention may be used to control bleeding disorders which have several causes such as clotting factor deficiencies (e.g. haemophilia A and B or deficiency of coagulation factors XI or VII) or clotting factor inhibitors, or they may be used to control excessive bleeding occurring in subjects with a normally functioning blood clotting cascade (no clotting factor deficiencies or inhibitors against any of the coagulation factors). The bleedings may be caused by a defective platelet function, thrombocytopenia or von Willebrand's disease. They may also be seen in subjects in whom an increased fibrinolytic activity has been induced by various stimuli.

In subjects who experience extensive tissue damage in association with surgery or vast trauma, the haemostatic mechanism may be overwhelmed by the demand of immediate haemostasis and they may develop bleedings in spite of a normal haemostatic mechanism. Achieving satisfactory haemostasis is also a problem when bleedings occur in organs such as the brain, inner ear region and eyes and may also be a problem in cases of diffuse bleedings (haemorrhagic gastritis and profuse uterine bleeding) when it is difficult to identify the source. The same problem may arise in the process of taking biopsies from various organs (liver, lung, tumour tissue, gastrointestinal tract) as well as in laparoscopic surgery. These situations share the difficulty of providing haemostasis by surgical techniques (sutures, clips, etc.). Acute and profuse bleedings may also occur in subjects on anticoagulant therapy in whom a defective haemostasis has been induced by the therapy given. Such subjects may need surgical interventions in case the anticoagulant effect has to be counteracted rapidly. Another situation that may cause problems in the case of unsatisfactory haemostasis is when subjects with a normal haemostatic mechanism are given anticoagulant therapy to prevent thromboembolic disease. Such therapy may include heparin, other forms of proteoglycans, warfarin or other forms of vitamin K-antagonists as well as aspirin and other platelet aggregation inhibitors.

A systemic activation of the coagulation cascade may lead to disseminated intravascular coagulation (DIC). However, such complications have not been seen in subjects treated with high doses of recombinant FVIIa because of a localised haemostatic process of the kind induced by the complex formation between FVIIa and TF exposed at the site of vessel wall injury. The Factor VII variants according to the invention may thus also be used in their activated form to control such excessive bleedings associated with a normal haemostatic mechanism.

For treatment in connection with deliberate interventions, the Factor VII variants of the invention will typically be administered within about 24 hours prior to performing the intervention, and for as much as 7 days or more thereafter. Administration as a coagulant can be by a variety of routes as described herein.

The dose of the Factor VII variants ranges from about 0.05 mg to 500 mg/day, preferably from about 1 mg to 200 mg/day, and more preferably from about 10 mg to about 175 mg/day for a 70 kg subject as loading and maintenance doses, depending on the weight of the subject and the severity of the condition.

The pharmaceutical compositions are primarily intended for parenteral administration for prophylactic and/or therapeutic treatment. Preferably, the pharmaceutical compositions are administered parenterally, i.e., intravenously, subcutaneously, or intramuscularly, or it may be administered by continuous or pulsatile infusion. The compositions for parenteral administration comprise the Factor VII variant of the invention in combination with, preferably dissolved in, a pharmaceutically acceptable carrier, preferably an aqueous carrier. A variety of aqueous carriers may be used, such as water, buffered water, 0.4% saline, 0.3% glycine and the like. The Factor VII variants of the invention can also be formulated into liposome preparations for delivery or targeting to the sites of injury. Liposome preparations are generally described in, e.g., U.S. Pat. No. 4,837,028, U.S. Pat. No. 4,501,728, and U.S. Pat. No. 4,975,282. The compositions may be sterilised by conventional, well-known sterilisation techniques. The resulting aqueous solutions may be packaged for use or filtered under aseptic conditions and lyophilised, the lyophilised preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The concentration of Factor VII variant in these formulations can vary widely, i.e., from less than about 0.5% by weight, usually at or at least about 1% by weight to as much as 15 or 20% by weight and will be selected primarily by fluid volumes, viscosities, etc., in accordance with the particular mode of administration selected.

Thus, a typical pharmaceutical composition for intravenous infusion could be made up to contain 250 ml of sterile Ringer's solution and 10 mg of the Factor VII variant. Actual methods for preparing parenterally administrable compositions will be known or apparent to those skilled in the art and are described in more detail in, for example, *Remington's Pharmaceutical Sciences*, 18th ed., Mack Publishing Company, Easton, Pa. (1990).

The compositions containing the Factor VII variants of the present invention can be administered for prophylactic and/or therapeutic treatments. In therapeutic applications, compositions are administered to a subject already suffering from a disease, as described above, in an amount sufficient to cure, alleviate or partially arrest the disease and its complications. An amount adequate to accomplish this is defined as "therapeutically effective amount". As will be understood by the person skilled in the art amounts effective for this purpose will depend on the severity of the disease or injury as well as the weight and general state of the subject. In general, however, the effective amount will range from about 0.05 mg up to about 500 mg of the Factor VII variant per day for a 70 kg subject, with dosages of from about 1.0 mg to about 200 mg of the Factor VII variant per day being more commonly used.

It must be kept in mind that the materials of the present invention may generally be employed in serious disease or injury states, that is, life threatening or potentially life threatening situations. In such cases, in view of the minimisation of extraneous substances and general lack of immunogenicity of human Factor VII variants in humans, it is possible and may be felt desirable by the treating physician to administer a substantial excess of these variant Factor VII compositions.

In prophylactic applications, compositions containing the Factor VII variant of the invention are administered to a subject susceptible to or otherwise at risk of a disease state or injury to enhance the subject's own coagulative capability. Such an amount is defined to be a "prophylactically effective dose." In prophylactic applications, the precise amounts once again depend on the subject's state of health and weight, but the dose generally ranges from about 0.05 mg to about 500 mg per day for a 70-kilogram subject, more commonly from about 1.0 mg to about 200 mg per day for a 70-kilogram subject.

Single or multiple administrations of the compositions can be carried out with dose levels and patterns being selected by the treating physician. For ambulatory subjects requiring daily maintenance levels, the Factor VII variants may be administered by continuous infusion using e.g. a portable pump system.

Local delivery of the Factor VII variant of the present invention, such as, for example, topical application may be carried out, for example, by means of a spray, perfusion, double balloon catheters, stent, incorporated into vascular grafts or stents, hydrogels used to coat balloon catheters, or other well established methods. In any event, the pharmaceutical compositions should provide a quantity of Factor VII variant sufficient to effectively treat the subject.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

The terminology for amino acid substitutions used the following examples are as follows. The first letter represent the amino acid naturally present at a position of SEQ ID NO:1. The following number represent the position in SEQ ID NO:1. The second letter represent the different amino acid substituting for (replacing) the natural amino acid. An example is M298Q, where an methionine at position 298 of SEQ ID NO:1 is replaced by a glutamine. In another example, V158T/M298Q, the valine in position 158 of SEQ ID NO:1 is replaced by a threonine and the methionine in position 298 of SEQ ID NO:1 is replaced by a Glutamine in the same Factor VII polypeptide.

Example 1

DNA Encoding [V158T/M298Q]-FVII, [K157A]-FVII, [E296V]-FVII, [E296V/M298Q]-FVII and [V158D/E296V]-FVII, [V158D/M298Q]-FVII, [V158D/M298K]-FVII, [V158D/E296V/M298Q]-FVII, [M298Q]-FVII, [S336G]-FVII, [K337A]-FVII, [V158D/E296V/M2980/K337A]-FVII A DNA construct encoding [V158T/M298Q]-FVII, [K157A]-FVII, [E296V]-FVII, [E296V/M298Q]-FVII and [V158D/E296V]-FVII, [V158D/M298Q]-FVII, [V158D/M298K]-FVII, [V158D/E296V/M298Q]-FVII, [M298Q]-FVII, [V158D/E296V/M298Q/K337A]-FVII, [S336G]-FVII, and [K337A]-FVII were prepared by site-directed mutagenesis using a supercoiled, double stranded DNA vector with an insert of interest and two synthetic primers containing the desired mutation. The following primer pairs were used:

```
For [K157A]-FVII:
5'-CCG AAT TGT GGG GGG CGC GGT GTG CCC CAA AGG G-3'    (SEQ ID NO:2)

5'-CCC TTT GGG GCA CAC CGC GCC CCC CAC AAT TCG G-3'    (SEQ ID NO:3)

For [V158D]-FVII:
5'-GTG GGG GGC AAG GAG TGC CCC AAA GGG G-3'            (SEQ ID NO:4)

5'-CCC CTT TGG GGC AGT CCT TGC CCC CCA C-3'            (SEQ ID NO:5)

For [V158T]-FVII:
5'-GTG GGG GGC AAG ACG TGC CCC AAA GGG G-3'            (SEQ ID NO:6)

5'-CCC CTT TGG GGC ACG TCT TGC CCC CCA C-3'            (SEQ ID NO:7)

For [E296V/M298Q]-FVII:
5'-GCC ACG GCC CTG GTG CTC CAG GTC CTC AAC GTG CCC-3'  (SEQ ID NO:8)

5'-GGG CAC GTT GAG GAC CTG GAG CAC CAG GGC CGT GGC-3'  (SEQ ID NO:9)

For [M298Q]-FVII:
5'-GCC CTG GAG CTC CAG GTC CTC AAC GTG CCC-3'          (SEQ ID NO:10)

5'-GGG CAC GTT GAG GAC CTG GAG CTC CAG GGC-3'          (SEQ ID NO:11)

For [M298K]-FVII:
5'-GCC CTG GAG CTC AAG GTC CTC AAC GTG-3'              (SEQ ID NO:12)

5'-CAC CTT GAG GAC CTT GAG CTC CAG GGC-3'              (SEQ ID NO:13)

For [S336G]-FVII:
5'-GGC TAC TCG GAT GGC GGC AAG GAC TCC TGC AAG-3'      (SEQ ID NO:14)

5'-CTT GCA GGA GTC CTT GCC GCC ATC CGA GTA GCC-3'      (SEQ ID NO:15)

For [K337A]-FVII:
5'-CGG ATG GCA GCG CGG ACT CCT GCA AGG G-3'            (SEQ ID NO:16)

5'-CCC TTG CAG GAG TCC GCG CTG CCA TCC G-3'            (SEQ ID NO:17)
```

The oligonucleotide primers, each complementary to opposite strands of the vector, were extended during temperature cycling by means of Pfu DNA polymerase. On incorporation of the primers, a mutated plasmid containing staggered nicks was generated. Following temperature cycling, the product was treated with DpnI which is specific for methylated and hemimethylated DNA to digest the parental DNA template and to select for mutation-containing synthesized DNA.

Procedures for preparing a DNA construct using polymerase chain reaction using specific primers are well known to persons skilled in the art (cf. *PCR Protocols,* 1990, Academic Press, San Diego, Calif., USA).

Example 2

Preparation of [V158T/M298Q]-FVII

BHK cells were transfected essentially as previously described (Thim et al. (1988) Biochemistry 27, 7785-7793; Persson and Nielsen (1996) FEBS Lett. 385, 241-243) to obtain expression of the variant [V158T/M298Q]-FVII. The Factor VII variant was purified as follows:

Conditioned medium was loaded onto a 25-ml column of Q SEPHAROSE™ Fast Flow (Pharmacia Biotech) after addition of 5 mM EDTA, 0.1% TRITON X-100® and 10 mM Tris, adjustment of pH to 8.0 and adjustment of the conductivity to 10-11 mS/cm by adding water. Elution of the protein was accomplished by stepping from 10 mM Tris, 50 mM NaCl, 0.1% TRITON X-100®, pH 8.0 to 10 mM Tris, 50 mM NaCl, 25 mM $CaCl_2$, 0.1% TRITON X-100®, pH 8.0. The fractions containing [V158T/M298Q]-FVII were pooled and applied to a 25-ml column containing monoclonal antibody F1A2 (Novo Nordisk, Bagsværd, Denmark) coupled to CNBr-activated SEPHAROSE™ 4B (Pharmacia Biotech). The column was equilibrated with 50 mM Hepes, pH 7.5, containing 10 mM $CaCl_2$, 100 mM NaCl and 0.02% TRITON X-100®. After washing with equilibration buffer and equilibration buffer containing 2 M NaCl, bound material was eluted with equilibration buffer containing 10 mM EDTA instead of $CaCl_2$. Before use or storage, excess $CaCl_2$ over EDTA was added or [V158T/M298Q]-FVII was transferred to a $Ca^{2+}$-containing buffer. The yield of each step was followed by factor VII ELISA measurements and the purified protein was analysed by SDS-PAGE.

Example 3

Preparation of [K157A]-FVII

BHK cells were transfected essentially as previously described (Thim et al. (1988) Biochemistry 27, 7785-7793; Persson and Nielsen (1996) FEBS Lett. 385, 241-243) to obtain expression of the variant [K157A]-FVII. The Factor VII variant was purified as follows:

Conditioned medium was loaded onto a 25-ml column of Q SEPHAROSE™ Fast Flow (Pharmacia Biotech) after addition of 5 mM EDTA, 0.1% TRITON X-100® and 10 mM Tris, adjustment of pH to 8.0 and adjustment of the conductivity to 10-11 mS/cm by adding water. Elution of the protein was accomplished by stepping from 10 mM Tris, 50 mM NaCl, 0.1% TRITON X-100®, pH 8.0 to 10 mM Tris, 50 mM NaCl, 25 mM $CaCl_2$, 0.1% TRITON X-100®, pH 8.0. The factions containing [K157A]-FVII were pooled and applied to a 25-ml column containing monoclonal antibody F1A2 (Novo Nordisk, Bagsværd, Denmark) coupled to CNBr-activated SEPHAROSE™ 4B (Pharmacia Biotech). The column was equilibrated with 50 mM Hepes, pH 7.5, containing 10 mM $CaCl_2$, 100 mM NaCl and 0.02% TRITON X-100®. After washing with equilibration buffer and equilibration buffer containing 2 M NaCl, bound material was eluted with equilibration buffer containing 10 mM EDTA instead of $CaCl_2$. Before use or storage, excess $CaCl_2$ over EDTA was added or [K157A]-FVII was transferred to a $Ca^{2+}$-containing buffer. The yield of each step was followed by factor VII ELISA measurements and the purified protein was analysed by SDS-PAGE.

Example 4

Preparation of [V158D/M298Q]-FVII

BHK cells were transfected essentially as previously described (Thim et al. (1988) Biochemistry 27, 7785-7793; Persson and Nielsen (1996) FEBS Lett. 385, 241-243) to obtain expression of the variant [V158D/M298Q]-FVII. The Factor VII variant was purified as follows:

Conditioned medium was loaded onto a 25-ml column of Q SEPHAROSE™ Fast Flow (Pharmacia Biotech) after addition of 5 mM EDTA, 0.1% TRITON X-100® and 10 mM Tris, adjustment of pH to 8.0 and adjustment of the conductivity to 10-11 mS/cm by adding water. Elution of the protein was accomplished by stepping from 10 mM Tris, 50 mM NaCl, 0.1% TRITON X-100®, pH 8.0 to 10 mM Tris, 50 mM NaCl, 25 mM $CaCl_2$, 0.1% TRITON X-100®, pH 8.0. The fractions containing [V158D/M298Q]-FVII were pooled and applied to a 25-ml column containing monoclonal antibody F1A2 (Novo Nordisk, Bagsværd, Denmark) coupled to CNBr-activated SEPHAROSE™ 4B (Pharmacia Biotech). The column was equilibrated with 50 mM Hepes, pH 7.5, containing 10 mM $CaCl_2$, 100 mM NaCl and 0.02% TRITON X-100®. After washing with equilibration buffer and equilibration buffer containing 2 M NaCl, bound material was eluted with equilibration buffer containing 10 mM EDTA instead of $CaCl_2$. Before use or storage, excess $CaCl_2$ over EDTA was added or [V158D/M298Q]-FVII was transferred to a $Ca^{2+}$-containing buffer. The yield of each step was followed by factor VII ELISA measurements and the purified protein was analysed by SDS-PAGE.

Example 5

Preparation of [V158D/M298K]-FVII

BHK cells were transfected essentially as previously described (Thim et al. (1988) Biochemistry 27, 7785-7793; Persson and Nielsen (1996) FEBS Lett. 385, 241-243) to obtain expression of the variant [V158D/M298K]-FVII. The Factor VII variant was purified as follows:

Conditioned medium was loaded onto a 25-ml column of Q SEPHAROSE™ Fast Flow (Pharmacia Biotech) after addition of 5 mM EDTA, 0.1% TRITON X-100® and 10 mM Tris, adjustment of pH to 8.0 and adjustment of the conductivity to 10-11 mS/cm by adding Water. Elution of the protein was accomplished by stepping from 10 mM Tris, 50 mM NaCl, 0.1% TRITON X-100®, pH 8.0 to 10 mM Tris, 50 mM NaCl, 25 mM $CaCl_2$, 0.1% TRITON X-100®, pH 8.0. The fractions containing [V158D/M298K]-FVII were pooled and applied to a 25-ml column containing monoclonal antibody F1A2 (Novo Nordisk, Bagsværd, Denmark) coupled to CNBr-activated SEPHAROSE™ 4B (Pharmacia Biotech). The column was equilibrated with 50 mM Hepes, pH 7.5, containing 10 mM $CaCl_2$, 100 mM NaCl and 0.02% TRITON X-100®. After washing with equilibration buffer and equilibration buffer containing 2 M NaCl, bound material was eluted with equilibration buffer containing 10 mM EDTA instead of $CaCl_2$. Before use or storage, excess $CaCl_2$ over EDTA was added or [V158D/M298K]-FVII was transferred to a $Ca^{2+}$-containing buffer. The yield of each step was followed by factor VII ELISA measurements and the purified protein was analysed by SDS-PAGE.

Example 6

Preparation of [V158D/E296V/M298Q]-FVII

BHK cells were transfected essentially as previously described (Thim et al. (1988) Biochemistry 27, 7785-7793; Persson and Nielsen (1996) FEBS Lett. 385, 241-243) to obtain expression of the variant [V158D/E296V/M298Q]-FVII. The Factor VII variant was purified as follows:

Conditioned medium was loaded onto a 25-ml column of Q SEPHAROSE™ Fast Flow (Pharmacia Biotech) after addition of 5 mM EDTA, 0.1% TRITON X-100® and 10 mM Tris, adjustment of pH to 8.0 and adjustment of the conductivity to 10-11 mS/cm by adding water. Elution of the protein was accomplished by stepping from 10 mM Tris, 50 mM NaCl, 0.1% TRITON X-100®, pH 8.0 to 10 mM Tris, 50 mM NaCl, 25 mM $CaCl_2$, 0.1% TRITON X-100®, pH 8.0. The fractions containing [V158D/E296V/M298Q]-FVII were pooled and applied to a 25-ml column containing monoclonal antibody F1A2 (Novo Nordisk, Bagsværd, Denmark) coupled to CNBr-activated SEPHAROSE™ 4B (Pharmacia Biotech). The column was equilibrated with 50 mM Hepes, pH 7.5, containing 10 mM $CaCl_2$, 100 mM NaCl and 0.02% TRITON X-100®. After washing with equilibration buffer and equilibration buffer containing 2 M NaCl, bound material was eluted with equilibration buffer containing 10 mM EDTA instead of $CaCl_2$. Before use or storage, excess $CaCl_2$ over EDTA was added or [V158D/E296V/M298Q]-FVII was transferred to a $Ca^{2+}$-containing buffer. The yield of each step was followed by factor VII ELISA measurements and the purified protein was analysed by SDS-PAGE.

Example 7

Preparation of [M298Q]-FVII

BHK cells were transfected essentially as previously described (Thim et al. (1988) Biochemistry 27, 7785-7793; Persson and Nielsen (1996) FEBS Lett. 385, 241-243) to obtain expression of the variant [M298Q]-FVII. The Factor VII variant was purified as follows:

Conditioned medium was loaded onto a 25-ml column of Q SEPHAROSE™ Fast Flow (Pharmacia Biotech) after addition of 5 mM EDTA, 0.1% TRITON X-100® and 10 mM Tris, adjustment of pH to 8.0 and adjustment of the conductivity to 10-11 mS/cm by adding water. Elution of the protein was accomplished by stepping from 10 mM Tris, 50 mM NaCl, 0.1% TRITON X-100®, pH 8.0 to 10 mM Tris, 50 mM NaCl, 25 mM $CaCl_2$, 0.1% TRITON X-100®, pH 8.0. The fractions containing [M298Q]-FVII were pooled and applied to a 25-ml column containing monoclonal antibody F1A2 (Novo Nordisk, Bagsværd, Denmark) coupled to CNBr-activated SEPHAROSE™ 4B (Pharmacia Biotech). The column was equilibrated with 50 mM Hepes, pH 7.5, containing 10 mM $CaCl_2$, 100 mM NaCl and 0.02% TRITON X-100®. After washing with equilibration buffer and equilibration buffer containing 2 M NaCl, bound material was eluted with equilibration buffer containing 10 mM EDTA instead of $CaCl_2$. Before use or storage, excess $CaCl_2$ over EDTA was added or [M298Q]-FVII was transferred to a $Ca^{2+}$-containing buffer. The yield of each step was followed by factor VII ELISA measurements and the purified protein was analysed by SDS-PAGE.

Example 8

Preparation of [S336G]-FVII

BHK cells were transfected essentially as previously described (Thim et al. (1988) Biochemistry 27, 7785-7793; Persson and Nielsen (1996) FEBS Lett. 385, 241-243) to obtain expression of the variant [S336G]-FVII. The Factor VII variant was purified as follows:

Conditioned medium was loaded onto a 25-ml column of Q SEPHAROSE™ Fast Flow (Pharmacia Biotech) after addition of 5 mM EDTA, 0.1% TRITON X-100® and 10 mM Tris, adjustment of pH to 8.0 and adjustment of the conductivity to 10-11 mS/cm by adding water. Elution of the protein was accomplished by stepping from 10 mM Tris, 50 mM NaCl, 0.1% TRITON X-100®, pH 8.0 to 10 mM Tris, 50 mM NaCl, 25 mM $CaCl_2$, 0.1% TRITON X-100®, pH 8.0. The fractions containing [S336G]-FVII were pooled and applied to a 25-ml column containing monoclonal antibody F1A2 (Novo Nordisk, Bagsværd, Denmark) coupled to CNBr-activated SEPHAROSE™ 4B (Pharmacia Biotech). The column was equilibrated with 50 mM Hepes, pH 7.5, containing 10 mM $CaCl_2$, 100 mM NaCl and 0.02% TRITON X-100®. After washing with equilibration buffer and equilibration buffer containing 2 M NaCl, bound material was eluted with equilibration buffer containing 10 mM EDTA instead of $CaCl_2$. Before use or storage, excess $CaCl_2$ over EDTA was added or [S336G]-FVII was transferred to a $Ca^{2+}$-containing buffer. The yield of each step was followed by factor VII ELISA measurements and the purified protein was analysed by SDS-PAGE.

Example 9

Preparation of [K337A]-FVII

BHK cells were transfected essentially as previously described (Thim et al. (1988) Biochemistry 27, 7785-7793; Persson and Nielsen (1996) FEBS Lett. 385, 241-243) to obtain expression of the variant [K337A]-FVII. The Factor VII variant was purified as follows:

Conditioned medium was loaded onto a 25-ml column of Q SEPHAROSE™ Fast Flow (Pharmacia Biotech) after addition of 5 mM EDTA, 0.1% TRITON X-100® and 10 mM Tris, adjustment of pH to 8.0 and adjustment of the conductivity to 10-11 mS/cm by adding water. Elution of the protein was accomplished by stepping from 10 mM Tris, 50 mM NaCl, 0.1% TRITON X-100®, pH 8.0 to 10 mM Tris, 50 mM NaCl, 25 mM $CaCl_2$, 0.1% TRITON X-100®, pH 8.0. The fractions containing [K337A]-FVII were pooled and applied to a 25-ml column containing monoclonal antibody F1A2 (Novo Nordisk, Bagsværd, Denmark) coupled to CNBr-activated SEPHAROSE™ 4B (Pharmacia Biotech). The column was equilibrated with 50 mM Hepes, pH 7.5, containing 10 mM $CaCl_2$, 100 mM NaCl and 0.02% TRITON X-100®. After washing with equilibration buffer and equilibration buffer containing 2 M NaCl, bound material was eluted wit equilibration buffer containing 10 mM EDTA instead of $CaCl_2$. Before use or storage, excess $CaCl_2$ over EDTA was added or [K337A]-FVII was transferred to a $Ca^{2+}$-containing buffer. The yield of each step was followed by factor VII ELISA measurements and the purified protein was analysed by SDS-PAGE.

Example 10

Preparation of [V158D/E296V/M298Q/K337A]-FVII

BHK cells were transfected essentially as previously described (Thim et al. (1988) Biochemistry 27, 7785-7793; Persson and Nielsen (1996) FEBS Lett. 385, 241-243) to obtain expression of the variant [V158D/E296V/M298Q/K337A]-FVII. The Factor VII variant was purified as follows:

Conditioned medium was loaded onto a 25-ml column of Q SEPHAROSE™ Fast Flow (Pharmacia Biotech) after addition of 5 mM EDTA, 0.1% TRITON X-100® and 10 mM Tris, adjustment of pH to 8.0 and adjustment of the conductivity to 10-11 mS/cm by adding water. Elution of the protein was accomplished by stepping from 10 mM Tris, 50 mM NaCl, 0.1% TRITON X-100®, pH 8.0 to 10 mM Tris, 50 mM NaCl, 25 mM $CaCl_2$, 0.1% TRITON X-100®, pH 8.0. The fractions containing [V158D/E296V/M298Q/K337A]-FVII were pooled and applied to a 25-ml column containing monoclonal antibody F1A2 (Novo Nordisk, Bagsværd, Denmark) coupled to CNBr-activated SEPHAROSE™ 4B (Pharmacia Biotech). The column was equilibrated with 50 mM Hepes, pH 7.5, containing 10 mM $CaCl_2$, 100 mM NaCl and 0.02% TRITON X-100®. After washing with equilibration buffer and equilibration buffer containing 2 M NaCl, bound material was eluted with equilibration buffer containing 10 mM EDTA instead of $CaCl_2$. Before use or storage, excess $CaCl_2$ over IEDTA was added or [V158D/E296V/M298Q/K337A]-FVII was transferred to a $Ca^{2+}$-containing buffer. The yield of each step was followed by factor VII ELISA measurements and the purified protein was analysed by SDS-PAGE.

Example 11

In Vitro Hydrolysis Assay

Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM Hepes, pH 7.4, containing 0.1 M NaCl, 5 mM CaCl$_2$ and 1 mg/ml bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used to calculate the ratio between the activities of variant and wild-type Factor VIIa:

Ratio=($A_{405\ nm}$ Factor VIIa variant)/($A_{405\ nm}$ Factor VIIa wild-type).

Example 12

In Vitro Proteolysis Assay

Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 microL 50 mM Hepes, pH 7.4, containing 0.1 M NaCl, 5 mM CaCl$_2$ and 1 mg/ml bovine serum albumin, are incubated for 15 min. Factor X cleavage is then stopped by the addition of 50 microL 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used to calculate the ratio between the proteolytic activities of variant and wild-type Factor VIIa:

Ratio=($A_{405\ nm}$ Factor VIIa variant)/($A_{405\ nm}$ Factor VIIa wild-type).

Example 13

Relative Activities of FVIIa Variants Measured in the Assays Described in Examples 11 and 12

| Variant | Ratio in example 11 | Ratio in example 12 |
|---|---|---|
| K157A | 0.9 | Not determined |
| V158T/M298Q-FVIIa | 3.8 | 10 |
| V158D/M298Q-FVIIa | 2.0 | 2.7 |
| V158D/M298K-FVIIa | 0.3 | Not determined |
| V158D/E296V/M298Q-FVIIa | 7.8 | 28 |
| M298Q-FVIIa | 3.4 | 5.5 |
| V158D/E296V/M298Q/K337A-FVIIa | 11.0 | 47 |
| S336G-FVIIa | 0.6 | Not determined |
| K337A-FVIIa | 3.9 | 4.4 |
| wt-FVIIa | 1.0 | 1.0 |

---

The invention claimed is:

1. An isolated nucleic acid construct comprising a nucleotide sequence encoding a Factor VII polypeptide of SEQ ID NO:1, wherein said polypeptide comprises one or more substitutions selected from the group consisting of:
   (a) substitution of Val158 with any amino acid other than Ala;
   (b) substitution of Glu296 with any amino acid other than Ala; and
   (c) a combination of (a) and (b).

2. The nucleic acid construct of claim 1, wherein said construct is a vector.

3. A recombinant host cell transformed with the nucleic acid construct of claim 1.

4. The recombinant host cell of claim 3, wherein said cell is selected from the group consisting of CHO, BHK, and HEK cells.

5. A method for producing a Factor VII polypeptide, said method comprising (i) cultivating the cell of claim 3 in an appropriate growth medium under conditions allowing expression of the nucleic acid construct and (ii) recovering the resulting polypeptide from the medium.

6. The nucleic acid construct of claim 1, wherein said polypeptide further comprises at least one substitution selected from the group consisting of:
   (a) Lys157 with any amino acid other than Ala;
   (b) Lys337 with any amino acid other than Ala;
   (c) Asp334 with any amino acid other than Ala;
   (d) Ser336 with any amino acid other than Ala; and
   (e) any combination of (a) to (d).

7. An isolated nucleic acid construct comprising a nucleotide sequence encoding a Factor VII polypeptide of SEQ ID NO:1, wherein said polypeptide is selected from the group consisting of V158T+M298Q-FVII, E296V+M298Q-FVII, V158D+E296V-FVII, V158D+M298Q-FVII, and V158D+M298K-FVII.

8. An isolated nucleic acid construct comprising a nucleotide sequence encoding a Factor VII polypeptide of SEQ ID NO:1, wherein said polypeptide is V158D+E296V+M298Q-FVII.

9. A method for producing a Factor VII polypeptide, said method comprising (i) cultivating a cell comprising the nucleic acid construct of claim 6 in an appropriate growth medium under conditions allowing expression of the nucleic acid and (ii) recovering the resulting polypeptide from the medium.

10. A method for producing a Factor VII polypeptide, said method comprising (i) cultivating a cell comprising the nucleic acid construct of claim 7 in an appropriate growth medium under conditions allowing expression of the nucleic acid and (ii) recovering the resulting polypeptide from the medium.

11. A method for producing a Factor VII polypeptide, said method comprising (i) cultivating a cell comprising the nucleic acid construct of claim 8 in an appropriate growth medium under conditions allowing expression of the nucleic acid and (ii) recovering the resulting polypeptide from the medium.

* * * * *